US012055550B2

(12) United States Patent
Cooks et al.

(10) Patent No.: US 12,055,550 B2
(45) Date of Patent: *Aug. 6, 2024

(54) CHARGED MASS LABELING SYSTEM

(71) Applicant: Purdue Research Foundation, West Lafayette, IN (US)

(72) Inventors: Robert Graham Cooks, West Lafayette, IN (US); Zane Baird, West Lafayette, IN (US); Michael Pugia, Elkhart, IN (US); Adam Hollerbach, West Lafayette, IN (US); Stephen Ayrton, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 101 days.

This patent is subject to a terminal disclaimer.

(21) Appl. No.: 17/342,804

(22) Filed: Jun. 9, 2021

(65) Prior Publication Data

US 2021/0293826 A1 Sep. 23, 2021

Related U.S. Application Data

(63) Continuation of application No. 16/071,347, filed as application No. PCT/US2017/014320 on Jan. 20, 2017, now Pat. No. 11,061,035.

(Continued)

(51) Int. Cl.
*G01N 33/68* (2006.01)
*G01N 33/531* (2006.01)
*G01N 33/574* (2006.01)

(52) U.S. Cl.
CPC ....... *G01N 33/6848* (2013.01); *G01N 33/531* (2013.01); *G01N 33/5748* (2013.01); *G01N 33/574* (2013.01); *G01N 2560/00* (2013.01)

(58) Field of Classification Search
CPC .......... G01N 33/6848; G01N 33/531; G01N 33/5748; G01N 33/574; G01N 2560/00; C12Q 1/6872
See application file for complete search history.

(56) References Cited

U.S. PATENT DOCUMENTS 4,683,195 A 7/1987 Mullis et al.
5,182,213 A 1/1993 Genshaw et al.
(Continued)

FOREIGN PATENT DOCUMENTS

IN 101542291 A 9/2009
JP 2009-508135 A 2/2009
(Continued)

OTHER PUBLICATIONS

Aebersold, 2001, Mass Spectrometry in Proteomics, Chem. Rev., 101:269-295.
(Continued)

*Primary Examiner* — Shafiqul Haq
(74) *Attorney, Agent, or Firm* — Brown Rudnick LLP; Adam M. Schoen

(57) ABSTRACT

The invention generally relates to charged mass label compositions and methods of use thereof for detecting a target analyte in a sample. In certain aspects, the invention provides a charged mass label composition including an affinity reagent, and a mass label precursor bound to the affinity reagent. The mass label precursor includes a label binding unit and a mass label. The label binding unit reversibly binds the mass label to the affinity reagent. The mass label includes a charge unit and a mass label unit having a pre-defined mass-to-charge-value in a mass spectrum.

9 Claims, 10 Drawing Sheets

Related U.S. Application Data

(60) Provisional application No. 62/286,115, filed on Jan. 22, 2016.

(56) References Cited

U.S. PATENT DOCUMENTS

| | | | |
|---|---|---|---|
| 5,270,163 | A | 12/1993 | Gold et al. |
| 5,475,096 | A | 12/1995 | Gold et al. |
| 6,818,395 | B1 | 11/2004 | Quake et al. |
| 7,169,560 | B2 | 1/2007 | Lapidus et al. |
| 7,211,390 | B2 | 5/2007 | Rothberg et al. |
| 7,244,559 | B2 | 7/2007 | Rothberg et al. |
| 7,264,929 | B2 | 9/2007 | Rothberg et al. |
| 7,282,337 | B1 | 10/2007 | Harris |
| 7,323,305 | B2 | 1/2008 | Eamon et al. |
| 7,335,762 | B2 | 2/2008 | Rothberg et al. |
| 7,335,897 | B2 | 2/2008 | Takats et al. |
| 8,304,718 | B2 | 11/2012 | Ouyang et al. |
| 8,859,956 | B2 | 10/2014 | Ouyang et al. |
| 11,061,035 | B2* | 7/2021 | Cooks ............... G01N 33/6848 |
| 2002/0076739 | A1 | 6/2002 | Aebersold et al. |
| 2002/0132357 | A1 | 9/2002 | Schneider et al. |
| 2002/0150927 | A1 | 10/2002 | Matray et al. |
| 2002/0164629 | A1 | 11/2002 | Quake et al. |
| 2004/0259164 | A1* | 12/2004 | Gygi ................. G01N 33/6842 435/7.1 |
| 2005/0042625 | A1* | 2/2005 | Schmidt ................ C07H 21/00 435/6.12 |
| 2008/0233575 | A1 | 9/2008 | Harris et al. |
| 2009/0053817 | A1 | 2/2009 | Reid et al. |
| 2009/0075252 | A1 | 3/2009 | Harris et al. |
| 2009/0197257 | A1 | 8/2009 | Harris |
| 2010/0029495 | A1 | 2/2010 | Schaefer |
| 2010/0068819 | A1* | 3/2010 | Hoffmann .......... G01N 33/6848 530/300 |
| 2011/0294952 | A1 | 12/2011 | Petersen |
| 2012/0119079 | A1 | 5/2012 | Ouyang et al. |
| 2013/0280819 | A1 | 10/2013 | Cooks et al. |
| 2014/0224981 | A1 | 8/2014 | Owen et al. |
| 2014/0264004 | A1 | 9/2014 | Cooks et al. |
| 2016/0086781 | A1 | 3/2016 | Cooks et al. |

FOREIGN PATENT DOCUMENTS

| | | |
|---|---|---|
| JP | 2009-530310 A | 8/2009 |
| WO | 2000/011208 A1 | 3/2000 |
| WO | 2002/042427 A2 | 5/2002 |
| WO | 2009/102766 A1 | 8/2009 |
| WO | 2015/184321 A2 | 12/2015 |
| WO | 2017/053911 A1 | 3/2017 |

OTHER PUBLICATIONS

Beardsley, 2004, Fragmentation of Amidinated Peptide Ions, J. of the American Society for Mass Spectrometry, 15(2):158-167.
Braslavsky, 2003, Sequence information can be obtained from ssingle DNA molecules, PNAS, 100:3960-3964.
Carroll, 1975, Atmospheric Pressure Ionization Mass Spectrometry: Corona Discharge Ion Source for Use in Liquid Chromatograph-Mass Spectrometer-Computer Analytical System, Anal. Chem. 47:2369-2373.
Caruthers, 1985, Gene synthesis machines: DNA chemistry and its uses, Science 230:281-285.
Chinese Office Action issued in Chinese Application No. 201780018381.8, date of mailing: Apr. 2, 2021, 4 pages.
Chinese Office Action issued in Chinese Application No. 201780018381.8, date of mailing: Oct. 10, 2020, 6 pages.
Cody, 2005, Versatile New Ion Source for the Analysis of Materials in Open Air under Ambient Condition, Anal. Chem. 77:2297-2302.
Drmanac, 1998, Accurate sequencing by hybridization for DNA diagnostics and individual genomics, Nature Biotech, 16:54-58.
Fenn, 1989, Electrospray ionization for mass spectrometry of large biomolecules, Science, 246:64-71.
Gao, 2006, Handheld rectilinear ion trap mass spectrometer, Anal. Chem, 78(17):5994-6002.
Gao, 2006, Handheld Rectilinear Ion Trap Mass Spectrometer, Anal. Chem., 78:5994-6002.
Harada, 1993, Monoclonal antibody G6K12 specific for membrane-associated differentiation marker of human stratified squamous epithelia and squamous cell carcinoma, J. Oral Pathol. Med., 22(4):145-152.
Hendricks, 2014, Autonomous in-situ analysis and real-time chemical detection using a backpack miniature mass spectrometer: concept, instrumentation development, and performance, Anal. Chem., 86:2900-2908.
Inai, 1993, Immunohistochemical detection of an enamel protein-related epitope in rat bone at an early stage of osteogenesis, Histochemistry 99(5):335-362.
Kogelschatz, 2003, Dielectric-barrier Discharges: their History, Discharge Physics, and Industrial Applications, Plasma Chemistry and Plasma Processing, 23:1-46.
Kogelschatz, 2003, Plasma Chemistry and Plasma Processing, 23:1-46.
Laiko, 2000, Atmospheric Pressure Matrix-Assisted Laser Desoprtion/Ionization Mass Spectrometry, Analytical Chemistry, 72:652-657.
Li, 2014, Mini 12, Miniature Mass Spectrometer for Clinical and other Applications—Introduction and Characterization, Anal. Chem., 86:2909-2916.
Maxam, 1977, A new method for sequencing DNA, PNAS, 74:560-564.
Mulder, 1993, Characterization of Two Human Monoclonal Antibodies Reactive with HLA-B12 and HLA-B60, Respectively, Raised by in vitro Secondary Immunization of Peripheral Blood Lymphocytes, Hum. Immunol., 36 (3):186-192.
Office Action issued in Japanese Application No. 2018-538139, date of mailing: Sep. 2, 2020, 2 pages.
Sanger, 1977, DNA sequencing with chain-terminating inhibitors, PNAS, 72(12):5463-67.
Shiea, 2005, Electrospray-assisted laser desorption/ionization mass spectrometry for direct ambient analysis of solids, J. Rapid Commun. Mass Spectrom., 19:3701-3704.
Stauber, 1993, Rapid Generation of monoclonal antibody-secreting hybridomas against Afhrican horse sickness virus in vitro immunization and the fusion/cloning technique, J. Immunol. Methods, 161(2):157-168.
Suzuki, 2004, Design and Synthesis of Lableing Reagents (MS Probes) for Highly Sensitive Electrospray Ioniazation Mass Spectrometry and Their Application to the Detection of Carbonyl, Alcohol, Carboxylic Acid and Primary Amine Samples, Analytical Sciences, 20:475-482.
Takats, 2004, Mass spectrometry sampling under ambient conditions with desorption electrospray ionization, Science, 306:471-473.
Tanaka, 1988, Protein and polymer analyses up to m/z 100 000 by laser ionization time-of-flight mass spectrometry, Rapid Commun. Mass Spectrom., 2:151-153.
Venkateswaran, 1992, Production of Anti-Fibroblast Growth Factor Receptor Monoclonal Antibodies by In Vitro Immunization, Hybridoma, 11(6) 729-739.
Yamashita, 1984, Electrospray ion source. Another variation on the free-jet theme, J. Phys. Chem., 88:4451-4459.
Zhang, 2004, Prediction of Low-Energy Collision-Induced Dissociation Spectra of Peptides, Analytical Chemistry 76:3908-3922.
Zhang, 2005, Prediction of Low-Energy Collision-Induced Dissociation Spectra of Peptides with Three or More Charges, Analytical Chemistry, 77:6364-6373.

* cited by examiner

CHARGED MASS LABELING SYSTEM

RELATED APPLICATION

The present application is a continuation of U.S. nonprovisional application Ser. No. 16/071,347, filed Jul. 19, 2018, which is a 35 U.S.C. § 371 national phase application of PCT/US17/14320, filed Jan. 20, 2017, which claims the benefit of and priority to U.S. provisional patent application Ser. No. 62/286,115, filed Jan. 22, 2016, the content of each of which is incorporated by reference herein in its entirety.

FIELD OF THE INVENTION

The invention generally relates to charged mass label compositions and methods of use thereof for detecting a target analyte in a sample.

BACKGROUND

Assays have been developed that focus on analyzing rare molecules (e.g. proteins, nucleic acids, etc.) from bodily fluids for the presence of abnormalities, thus leading to early diagnosis of certain conditions such as cancer. In a typical bodily fluid sample however, a majority of the rare molecules are degraded, and any altered rare molecules containing an abnormality of interest are present in small amounts (e.g., less than 1%) relative to a total amount of molecules in the sample. This results in a failure to detect the small amount of abnormal rare molecules.

Affinity assays, nucleic acid assays, and cellular analysis assays have been developed for detection of rare molecules in a sample. Each has certain drawbacks. For example, the detection of rare molecules in the range of 1 to 50,000 copies per mL (femtomolar (fM) or less) cannot be achieved by conventional affinity assays, which require a number of molecular copies far above the numbers found for rare molecules. Immunoassays are limited by the affinity binding constant of an antibody, which is typically not higher than $10^{-12}$ (1 pM). Immunoassays require at least 100-fold antibody excess due to the off-rate being $10^{-13}$, and the solubility of the antibody protein limits driving the reaction to completion.

In the case of nucleic acids, amplification based approaches (e.g., polymerase chain reaction (PCR), digital PCR, quantitative PCR) have previously been employed to attempt to detect these abnormalities. However, due to the stochastic nature of the amplification reaction, a population of molecules that is present in a small amount in the sample often is overlooked. In fact, if a rare nucleic acid is not amplified in the first few rounds of amplification, it becomes increasingly unlikely that the rare species will ever be detected.

In cases in which the rare molecules are cell bound or included within the cell, cellular analysis techniques are employed, requiring isolation of cells of interest that include the rare molecule. Those cells including the rare molecule typically represent only a small fraction of a sample under analysis. Therefore, methods with high separation efficiency and cell recovery rates are necessary even before the detection of rare molecules within those cells. After purification, rare cells can be analyzed down to the single cell level by conventional scanning microscopy. However, even with automation of the scanning and analysis, the microscopy method can take 24 hours or more for each sample to be scanned. Additionally, all the rare cells with multiple images must be examined visually by the pathologist to determine the significance of measured amounts of protein.

Attempts have been made to use mass spectrometry (MS) for rare event detection. However, several issues have arisen. For example, an inability exists to separate markers of interest from sample interference (matrix overlap). Higher limit of detection due to background in a clinical sample (picomolar (pM) increased to nanomolar (nM)) is an issue. There is an inability to work with small nL, sample volumes as samples of less than 1 microliters (μl) are inefficiently captured for ionization and inefficiently isolated from complex samples such as blood. In addition, MS often has an inability to detect certain masses due to competition with other ions of the same mass being ionized or to suppression of ionization by the presence of particular matrix components. These issues typically cause problems due to false positive and/or negative results.

To address those issues, techniques have been developed that rely on using mass labels that bind to a rare molecule in a sample. That approach allows mass spectrometry to be used for rare event detection because using a mass label overcomes the above issues associated with direct detection of a rare molecule in a sample.

However, problems continue to exist with mass labels that have limited the full potential of mass spectrometry for rare molecule detection. For example, current MS labels typically utilize a peptide bound to an affinity agent by a reversible disulfide bond. However peptides tend to exchange protons easily in a mass spectrometer and generally have low ionization efficiencies. Additionally, the chemical used to release peptides from disulfide bonds, such as TCEP and DTT, may suppress the signal intensity in the mass spectrum from the mass label. While strong acids such as TFA may improve ionization efficiency, they prevent TCEP and DTT from cleaving disulfide bonds, thus separate liquids are needed for releasing and ionizing mass labels by spray-based ionization.

Therefore, problems still exist in the application of mass label technology; namely, mass labels such as peptides do not have ideal ionization efficiencies, current mass labels may not fragment into predictable masses separable from the background noise and mass labels are not readily cleaved from affinity reagents.

SUMMARY

The invention generally relates to charged mass label compositions designed to be analytically separated from background masses of the samples and that are ionized with high efficiency. The compositions of the invention include an affinity reagent, and a mass label precursor bound to the affinity reagent. Because of the specificity of the affinity reagent, each MS label can correspond to one or more target rare molecules from a sample. Multiple stage MS (a.k.a. $MS^n$, CID) can be used to detect different populations of rare molecules in a sample. The bound affinity agent is exposed to a substance to chemically release the MS label for MS analysis to determine the presence and/or amount of each different MS label. The presence and/or amount of each different MS label is related to the presence and/or amount of each different population of rare molecules in the sample.

The mass label precursor includes a label binding unit and a mass label. The label binding unit reversibly binds the mass label to the affinity reagent. The reversible binding of the label binding unit allows for easy and reliable cleavability of the MS label from the affinity agent. The mass label includes a charge unit (e.g., a pre-charged (ionic functional group) such as a quaternary ammonium (quaternary amine) group, or an analogous sulfonium or phosphonium cation, or pyridinium or imidzazolium). This charge unit is ionic and so is readily observed in the MS as a gas-phase ion. The mass label also includes a mass label unit having a pre-defined mass-to-charge-value in a mass spectrum. The mass label may generate at least one unique mass fragment due to fragmentation upon ionization and MS/MS into a least one predictable m/z separated from the background. Because the mass label produces a predictable m/z separated from the background, the characteristic mass label is readily detected by mass spectrometry.

Numerous different types of affinity reagents can be used in the compositions of the invention. In certain embodiments, the affinity reagent includes at least one member of a specific binding pair. The affinity reagent may be non-particulate or particulate and is linked to a mass spectrometry (MS) label precursor from which can release an entity that comprises the MS label. In certain embodiments, the mass label unit and the charge unit are bound to each other by one or more bonds that are resistant to breakage upon ionization. Typically, the label binding unit includes a reversible bond, such as an acetal or ketal bond.

The charge unit includes one or more chemical moieties arranged to have a charge upon ionization. For example, the charge unit may include one or more chemical moieties selected from the group consisting of formulas I-VII:

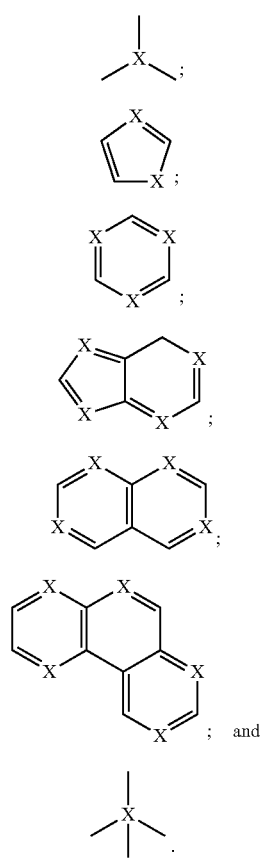

Formula I

Formula II

Formula III

Formula IV

Formula VI

Formula VI

Formula VII embodiments, at least one X is a quaternary ammonium cation or a quaternary phosphonium cation that is optionally substituted by at least one R. That R may be selected from the group consisting of hydrogen, alkyl, or an aromatic organic derivative. In other embodiments, the charge unit is a chemical moiety selected from the group consisting of: carnitine, imidazolium, pyridinium, tetra ethyl amine, benzalkonium amine, alkyl benzethonium amine, triphenyl phosphonium cation, and trialkyl(2,3-dihydroxypropyl).

The mass label unit may include an arrangement of chemical moieties that produce one or more fragments upon ionization. In such embodiments, at least one of the one or more fragments has a pre-defined mass-to-charge-value in a mass spectrum. In certain embodiments, the pre-defined mass-to-charge-value in the mass spectrum of the mass label or one or more fragments of the mass label is different from background mass-to-charge-values in the mass spectrum.

Other aspects of the invention include methods for detecting a target analyte in a sample. Such methods may involve introducing a charged mass label composition to a sample comprising a target analyte, wherein the charged mass label composition comprises an affinity reagent; and a mass label precursor bound to the affinity reagent, wherein the mass label precursor comprises a label binding unit and a mass label, the label binding unit reversibly binding the mass label to the affinity reagent, and wherein the mass label comprises a charge unit and a mass label unit having a pre-defined mass-to-charge-value in a mass spectrum. The methods then involve incubating the sample and the charged mass label composition so that the charged mass label composition binds the target analyte via an interaction between the affinity reagent of the charged mass label composition and the target analyte. The mass label is then released from the affinity reagent by breaking one or more bonds of the label binding unit. The mass label is ionized and the ionized mass label and/or fragments thereof are detected in a mass spectrometer, thereby detecting the target analyte in the sample. Methods of the invention may further involve quantifying the ionized mass label and/or fragments thereof, thereby quantifying the target analyte in the sample.

Methods of the invention may be used with various types of samples, such as biological samples, environmental samples, agricultural samples, etc. In certain embodiments, the target analyte is a target biological molecule. Typically, presence of the target biological molecule is indicative of a disease, such as cancer.

Other examples described herein are directed to methods of detecting one or more different populations of target rare molecules in a sample suspected of containing the one or more different populations of rare molecules and non-rare molecules by mass spectrometry (MS). The concentration of the one or more different populations of target rare molecules is detected over that of the non-rare molecules with an affinity agent that comprises a specific binding partner to a target rare molecule population of one of the populations of the rare molecules present. The affinity reagent may be non-particulate or particulate and is linked to a mass label precursor, which releases a mass label after exposure to a liquid containing a reagent that facilitates the breakage of the bond between the mass label and the label binding unit within the label precursor. The quaternary mass label is subjected to MS analysis to determine the presence and/or amount of each different quaternary mass label. The presence and/or amount of the quaternary mass label are related to the presence and/or amount of target rare molecules in the sample.

Another example described herein is directed to methods of detecting one or more different populations of target rare molecules in a sample suspected of containing one or more different populations of rare molecules and non-rare molecules by mass spectrometry (MS). The concentration of the one or more different populations of target rare molecules is detected over that of the non-rare molecules by bonding an affinity reagent linked to a mass label precursor to the target rare molecule. After the affinity reagent binds the rare molecule, mass labels are chemically released with a release reagent and are subjected to MS analysis to determine the presence and/or amount of quaternary mass label and, therefore, rare molecule. The presence and/or amount of the mass label is directly related to the presence and/or amount of target rare molecules in the sample.

DETAILED DESCRIPTION

The invention generally relates to charged mass label compositions and methods of use thereof for detecting a target analyte in a sample. In certain aspects, the invention provides a charged mass label composition including an affinity reagent, and a mass label precursor bound to the affinity reagent. The mass label precursor includes a label binding unit and a mass label. The label binding unit reversibly binds the mass label to the affinity reagent. The mass label includes a charge unit and a mass label unit having a pre-defined mass-to-charge-value in a mass spectrum.

Figure 1:
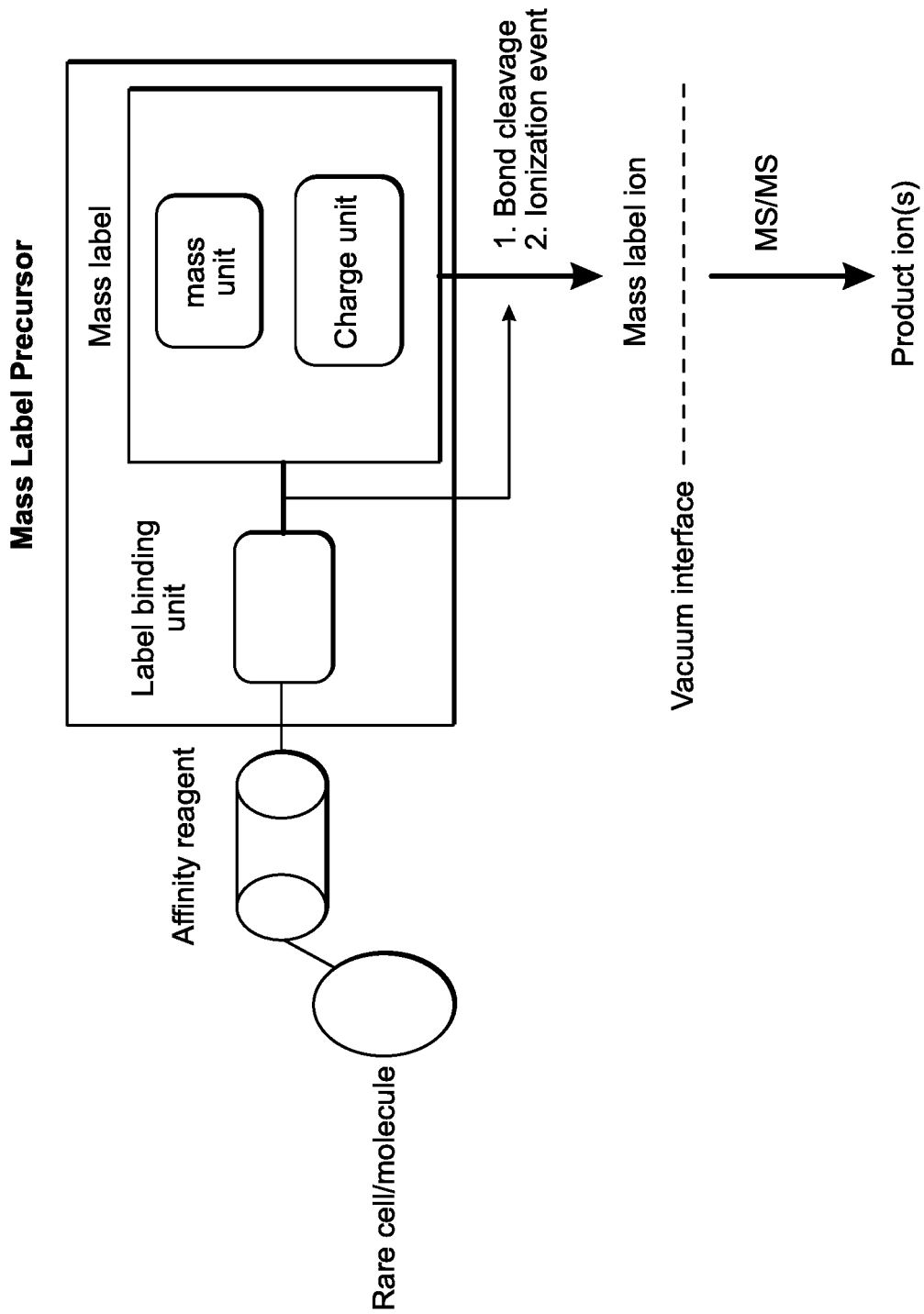
FIG. 1 is an illustration of one embodiment of the invention. A rare molecule/cell is bound to an affinity reagent which may be particulate or non-particulate. The affinity reagent in turn is functionalized with a label binding unit that facilitates reversible conjugation to a mass label. The mass label and label binding unit constitute the mass label precursor. The mass label is comprised of a charge unit (which bears a formal charge such as a quaternary ammonium, sulfonium or phosphonium salt) and a variable mass unit which is formally neutral and is varied to produce mass labels that appear at a pre-defined m/z value in the mass spectrum.

The mass label generates at least one unique fragment when subjected to MS/MS. This fragmentation is predictable and generates at least one mass that can be analytically separated from the background spectrum. The mass label ion may be generated by an ionization event in the ambient environment (FIG. 1). The mass label and its product ions are detected in the vacuum of the mass spectrometer (FIG. 1). The mass labels (e.g., quaternary mass labels) can be attached to an affinity reagent or rare molecule by a label binding unit (e.g., an acetal or ketal bond) and used for methods for detection of rare molecules.

Some examples are directed to methods of detecting one or more different populations of target rare molecules in a sample suspected of containing the one or more different populations of rare molecules and non-rare molecules by mass spectrometry (MS). The concentration of the one or more different populations of target rare molecules may be detected over that of the non-rare molecules by bonding a composition of the invention to the target rare molecule in the sample. The attachment may be done in a non-particulate or particulate bond between rare molecules and mass label precursor, which after exposure to a liquid with alteration agent releases the mass label from the rare molecule. The treated sample may be subjected to MS analysis to determine or quantify the presence and/or amount of quaternary mass label. The presence and/or amount of the mass label can be related to the presence and/or amount of target rare molecules in the sample.

The term "affinity reagent" refers to members of a specific binding pair. Examples include an immunological pair such as antigen-antibody or hapten-antibody, biotin-avidin pairs, hormones-hormone receptors, enzyme-substrate, nucleic acid duplexes, IgG-protein A, protein-nucleotide pair, and polynucleotide pairs such as DNA-DNA, DNA-RNA. For example a nucleic acid (e.g., polynucleotide) may be a "affinity reagent" that is complementary to a target nucleic acid. Polynucleotides refer to a polymeric form of nucleotides of any length, either deoxyribonucleotides or ribonucleotides, or analogues thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides such as, for example, methylated nucleotides and nucleotide analogues. If present, modifications to the nucleotide structure may be imparted before or after assembly of the polymer. The sequence of nucleotides may be interrupted by non-nucleotide components. A polynucleotide may be further modified, such as by conjugation with a labeling component. The composition of the affinity can include particles for amplification and capture which may be an entity of organic or inorganic, magnetic or non-magnetic materials.

In certain embodiments, the affinity reagent is a nucleic acid. In certain embodiments, the sequence of the target rare nucleic acid can be determined by reference to literature. For example, mutations that result in loss of genetic material that give rise to cancer, and their location within a gene are known in the art. See, e.g., Hesketh, The Oncogene Facts Book, Academic Press Limited (1995). Knowing the mutation and the location of the mutation, one of skill in the art can readily design a nucleic acid affinity reagent that will bind to a rare nucleic acid sequence in a sample.

Alternatively, samples from the subject may be obtained and sequenced in order to determine the sequence of the rare nucleic acid in the sample. Typically, a sample is obtained from a subject. The sample may be obtained in any clinically acceptable manner, and the nucleic acids are extracted from the sample by methods known in the art. Generally, nucleic acid can be extracted from a biological sample by a variety of techniques such as those described by Maniatis, et al. (Molecular Cloning: A Laboratory Manual, Cold Spring Harbor, N.Y., pp. 280-281, 1982), the contents of which are incorporated by reference herein in their entirety.

Once obtained, the nucleic acid molecules are sequenced by any method known in the art, e.g., ensemble sequencing or single molecule sequencing. One conventional method to perform sequencing is by chain termination and gel separation, as described by Sanger et al., Proc Natl Acad Sci USA. 74(12): 5463 67 (1977). Another conventional sequencing method involves chemical degradation of nucleic acid fragments. See, Maxam et al., Proc. Natl. Acad. Sci., 74: 560 564 (1977). Finally, methods have been developed based upon sequencing by hybridization. Sec, e.g., Drmanac, et al. (Nature Biotech., 16: 54 58, 1998). The contents of each of reference is incorporated by reference herein in its entirety.

In certain embodiments, sequencing is performed by the Sanger sequencing technique. Classical Sanger sequencing involves a single-stranded DNA template, a DNA primer, a DNA polymerase, radioactively or fluorescently labeled nucleotides, and modified nucleotides that terminate DNA strand elongation. If the label is not attached to the dideoxynucleotide terminator (e.g., labeled primer), or is a monochromatic label (e.g., radioisotope), then the DNA sample is divided into four separate sequencing reactions, containing four standard deoxynucleotides (dATP, dGTP, dCTP and dTTP) and the DNA polymerase. To each reaction is added only one of the four dideoxynucleotides (ddATP, ddGTP, ddCTP, or ddTTP). These dideoxynucleotides are the chain-terminating nucleotides, lacking a 3'—OH group required for the formation of a phosphodiester bond between two nucleotides during DNA strand elongation. If each of the dideoxynucleotides carries a different label, however, (e.g., 4 different fluorescent dyes), then all the sequencing reactions can be carried out together without the need for separate reactions.

Incorporation of a dideoxynucleotide into the nascent, i.e., elongating, DNA strand terminates DNA strand extension, resulting in a nested set of DNA fragments of varying length. Newly synthesized and labeled DNA fragments are denatured, and separated by size using gel electrophoresis on a denaturing polyacrylamide-urea gel capable of resolving single-base differences in chain length. If each of the four DNA synthesis reactions was labeled with the same, monochromatic label (e.g., radioisotope), then they are separated in one of four individual, adjacent lanes in the gel, in which each lane in the gel is designated according to the dideoxynucleotide used in the respective reaction, i.e., gel lanes A. T. G, C. If four different labels were utilized, then the reactions can be combined in a single lane on the gel. DNA bands are then visualized by autoradiography or fluorescence, and the DNA sequence can be directly read from the X-ray film or gel image.

The terminal nucleotide base is identified according to the dideoxynucleotide that was added in the reaction resulting in that band or its corresponding direct label. The relative positions of the different bands in the gel are then used to read (from shortest to longest) the DNA sequence as indicated. The Sanger sequencing process can be automated using a DNA sequencer, such as those commercially available from PerkinElmer. Beckman Coulter. Life Technologies, and others.

In other embodiments, sequencing of the nucleic acid is accomplished by a single-molecule sequencing by synthesis technique. Single molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslavsky, et al., PNAS (USA), 100: 3960-3964 (2003), the contents of each of these references is incorporated by reference herein in its entirety. Briefly, a single-stranded nucleic acid (e.g., DNA or cDNA) is hybridized to oligonucleotides attached to a surface of a flow cell. The oligonucleotides may be covalently attached to the surface or various attachments other than covalent linking as known to those of ordinary skill in the art may be employed. Moreover, the attachment may be indirect, e.g., via a polymerase directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

Other single molecule sequencing techniques involve detection of pyrophosphate as it is cleaved from incorporation of a single nucleotide into a nascent strand of DNA, as is shown in Rothberg et al. (U.S. Pat. Nos. 7,335,762, 7,264,929, 7,244,559, and 7,211,390) and Leamon et al. (U.S. Pat. No. 7,323,305), the contents of each of which is incorporated by reference herein in its entirety.

In other embodiments, targeted resequencing is used. Resequencing is shown for example in Harris (U.S. patent application numbers 2008/0233575, 2009/0075252, and 2009/0197257), the contents of each of which are incorporated by reference herein in their entirety. Briefly, a specific segment of the target is selected (for example by PCR, microarray, or MIPS) prior to sequencing. A primer designed to hybridize to this particular segment, is introduced and a primer/template duplex is formed. The primer/template duplex is exposed to a polymerase, and at least one detectably labeled nucleotide under conditions sufficient for template dependent nucleotide addition to the primer. The incorporation of the labeled nucleotide is determined, as well the identity of the nucleotide that is complementary to a nucleotide on the template at a position that is opposite the incorporated nucleotide. After the polymerization reaction, the primer may be removed from the duplex. The primer may be removed by any suitable means, for example by raising the temperature of the surface or substrate such that the duplex is melted, or by changing the buffer conditions to destabilize the duplex, or combination thereof. Methods for melting template/primer duplexes are well known in the art and are described, for example, in chapter 10 of Molecular Cloning, a Laboratory Manual, 3.sup.rd Edition, J. Sambrook, and D. W. Russell, Cold Spring Harbor Press (2001), the teachings of which are incorporated herein by reference.

After removing the primer, the template may be exposed to a second primer capable of hybridizing to the template. In one embodiment, the second primer is capable of hybridizing to the same region of the template as the first primer (also referred to herein as a first region), to form a template/primer duplex. The polymerization reaction is then repeated, thereby resequencing at least a portion of the template.

If the nucleic acid from the sample is degraded or only a minimal amount of nucleic acid can be obtained from the sample, PCR can be performed on the nucleic acid in order to obtain a sufficient amount of nucleic acid for sequencing (See e.g., Mullis et al. U.S. Pat. No. 4,683,195, the contents of which are incorporated by reference herein in its entirety).

Once the sequence of the rare nucleic acid is known, the nucleic acid affinity reagent can be synthesized using nucleic acid synthesis techniques that are routine in the art. Methods of synthesizing oligonucleotide are known in the art. See, e.g., Sambrook et al. (DNA microarray: A Molecular Cloning Manual, Cold Spring Harbor, N. Y., 2003) or Maniatis, et al. (Molecular Cloning: A Laboratory Manual, Cold Spring Harbor, N.Y., 1982), the contents of each of which are incorporated by reference herein in their entirety. Suitable methods for synthesizing oligonucleotide are also described in Caruthers (Science 230:281-285, 1985), the contents of which are incorporated by reference. Oligonucleotides can also be obtained from commercial sources such as Operon Technologies, Amersham Pharmacia Biotech, Sigma, and Life Technologies. The oligonucleotides can have an identical melting temperature. The lengths of the oligonucleotides can be extended or shortened at the 5' end or the 3' end to produce oligonucleotides with desired melting temperatures. Also, the annealing position of each oligonucleotide can be designed such that the sequence and length of the nucleic acid affinity reagent yields the desired melting temperature. The simplest equation for determining the melting temperature of nucleic acid affinity reagents smaller than 25 base pairs is the Wallace Rule (Td=2(A+T)+4(G+C)). Computer programs can also be used to design oligonucleotides, including but not limited to Array Designer Software (Arrayit Inc.). Oligonucleotide Probe Sequence Design Software for Genetic Analysis (Olympus Optical Co.). NetPrimer, and DNAsis from Hitachi Software Engineering. The TM (melting temperature) of each probe is calculated using software programs such as Oligo Design, available from Invitrogen Corp.

In other embodiments, the affinity reagent may be an antibody. The antigen against which the antibody binds may be determined from published literature. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4): 145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

In certain embodiments, the conjugate moiety is an aptamer. As used herein. "aptamer" and "nucleic acid ligand" are used interchangeably to refer to a nucleic acid that has a specific binding affinity for a target molecule, such as a protein. Like all nucleic acids, a particular nucleic acid ligand may be described by a linear sequence of nucleotides (A. U. T. C and G), typically 15-40 nucleotides long. Nucleic acid ligands can be engineered to encode for the complementary sequence of a target protein known to associate with the presence or absence of a specific disease.

In solution, the chain of nucleotides form intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the picomolar to low nanomolar range.

Aptamers used in the compositions of the invention depend upon the target tissue. Nucleic acid ligands may be discovered by any method known in the art. In one embodiment, nucleic acid ligands are discovered using an in vitro selection process referred to as SELEX (Systematic Evolution of Ligands by Exponential enrichment). See for example Gold et al. (U.S. Patent Numbers 5.270.163 and 5.475.096), the contents of each of which are herein incorporated by reference in their entirety. SELEX is an iterative process used to identify a nucleic acid ligand to a chosen molecular target from a large pool of nucleic acids. The process relies on standard molecular biological techniques, using multiple rounds of selection, partitioning, and amplification of nucleic acid ligands to resolve the nucleic acid ligands with the highest affinity for a target molecule. The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. There have been numerous improvements to the basic SELEX method, any of which may be used to discover nucleic acid ligands for use in methods of the invention.

A "rare molecule" refers to a molecule that is present in a sample in relatively small quantities when compared to the amount of non-rare molecules in a sample. In some examples, the rare molecules are present in an amount of about $10^{-8}\%$ to about $10^{-2}\%$ by weight of a total molecule population in a sample suspected of containing the rare molecules. The rare molecules may be, but are not limited to, cell-free circulating molecules or molecules found in rare cells, such as malignant cells such as malignant neoplasms or cancer cells; circulating endothelial cells; circulating epithelial cells; mesochymal cells; fetal cells; immune cells (B cells. T cells, macrophages, NK cells, monocytes); stem cells; nucleated red blood cells (normoblasts or crythroblasts); and immature granulocytes. Rare molecules are further described for example in PCT/US2016/053610, the content of which is incorporated by reference herein in its entirety.

Non-rare molecules are those molecules that are present in relatively large amounts when compared to the amount of rare molecules in a sample. In some examples, the non-rare molecules are at least about 10 times, or at least about 102 times, or at least about 103 times, or at least about 104 times, or at least about 105 times, or at least about 106 times, or at least about 107 times, or at least about 108 times greater than the amount of the rare molecules in the total molecular population in a sample suspected of containing non-rare molecules and rare molecules. The non-rare molecules may be cell-free circulating non-rare molecules or non-rare molecules found in a non-rare cell, such as, but are not limited to, white blood cells, platelets, and red blood cells.

The term "rare molecule" can include, but are not limited to, antigens, proteins, peptides, hormones, vitamins, allergens, autoimmune antigens, carbohydrates, lipids, glycoproteins, co-factors, antibodies, enzymes, enzyme substrates, metabolites, nucleic acids, antibodies, organic amines, fatty acids, carbohydrates, cyclic hydrocarbons, aliphatic hydrocarbons, aromatic hydrocarbons, organic carboxylic acids, organic amines, ceramines, cerebrosides, steroids, prostaglandins, carbohydrates, nucleosides and therapeutic drugs, for example and other biomolecules for example. Including biomolecules useful in medical diagnosis of diseases, which include, but are not limited to, biomarkers for detection of cancer, cardiac damage, cardiovascular disease, neurological disease, hemostasis/hemastasis, fetal maternal assessment, fertility, bone status, hormone levels, vitamins, allergies, autoimmune diseases, hypertension, kidney disease, diabetes, liver diseases, infectious diseases and other biomolecules useful in medical diagnosis of diseases, for example. The biomarkers for example can be from cells such as bacteria, virus, fungus, and protozoa; malignant cells such as malignant neoplasms or cancer cells; circulating endothelial cells; circulating tumor cells; circulating cancer stem cells; circulating cancer mesochymal cells; circulating epithelial cells; fetal cells; immune cells (B cells, T cells, macrophages. NK cells, monocytes); and stem cells.

Target rare molecules of rare cells include, but are not limited to, cancer cell type biomarkers, oncoproteins and oncogenes, chemo resistance biomarkers, metastatic potential biomarkers, and cell typing markers, for example. Cancer cell type biomarkers include, by way of illustration and not limitation, cytokeratins (CK) (CK1, CK2, CK3, CK4, CKS, CK6, CK7, CK8 and CK9, CK10, CK12, CK 13, CK14, CK16, CK17, CK18, CK19 and CK2), epithelial cell adhesion molecule (EpCAM), N-cadherin, E-cadherin and vimentin, for example.

Oncoproteins and oncogenes with likely therapeutic relevance due to mutations include, but are not limited to, WAF, BAX-1, PDGF, JAGGED 1, NOTCH, VEGF, VEGHR, CAIX, MIB1, MDM, PR, ER, SELS, SEM1, PI3K, AKT2, TWIST1, EML-4, DRAFF, C-MET, ABL1, EGFR, GNAS, MLH1, RET, MEK1, AKT1, ERBB2, HER2, HNFIA, MPL, SMAD4, ALK, ERBB4, HRAS, NOTCH1, SMARCB1, APC, FBXW7, IDH1, NPM1, SMO, ATM, FGFR1, JAK2, NRAS, SRC, BRAF, FGFR2, JAK3, RA, STK11, CDH1, FGFR3, KDR, PIK3CA, TP53, CDKN2A, FLT3, KIT, PTEN, VHL, CSFIR, GNA11, KRAS, PTPN11, DDR2, CTNNB1, GNAQ, MET, RB1, AKT1, BRAF, DDR2, MEK1, NRAS, FGFR1, and ROS1, for example.

Endothelial cell typing markers include, by way of illustration and not limitation, CD136, CD105/Endoglin, CD144/VE-cadherin, CD145, CD34, Cd41 CD136, CD34, CD90. CD31/PECAM-1, ESAM.VEGFR2/Fik-1. Tic-2, CD202b/TEK, CD56/NCAM, CD73/VAP-2, claudin 5, 20-1, and vimentin, for example.

Metastatic potential biomarkers include, but are limited to, urokinase plasminogen activator (uPA), plasminogen activator inhibitor (PAI-1), CD95, serine proteases (e.g., plasmin and ADAM, for example); serine protease inhibitors (e.g., Bikunin); matrix metalloproteinases (e.g., MMP9); matrix metalloproteinase inhibitors (e.g., TIMP-1). Chemoresistance biomarkers include, by way of illustration and not limitation, PL2L piwi like, 5T4, ADLH, β-integrin, α6 integrin, c-kit, c-met, LIF-R, CXCR4, ESA, CD 20, CD44, CD133, CKS, TRAF2 and ABC transporters, cancer cells that lack CD45 or CD31 but contain CD34 are indicative of a cancer stem cell; and cancer cells that contain CD44 but lack CD24.

In methods herein, white blood cells may be excluded as non-rare cells. For example, markers such as, but not limited to, CD45, CTLA-4, CD4, CD6S and CDS that are present on white blood cells can be used to indicate that a cell is not a rare cell of interest. In a particular non-limiting example, CD45 antigen (also known as protein tyrosine phosphatase receptor type C or PTPRC) and originally called leukocyte common antigen is useful in detecting all white blood cells.

Additionally, CD45 can be used to differentiate different types of white blood cells that might be considered rare cells. For example, granulocytes are indicated by CD45+. CD15+; monocytes are indicated by CD45+, CD14+; T lymphocytes are indicated by CD45+, CD3+; T helper cells are indicated by CD45+,CD3+, CD4+; cytotoxic T cells are indicated by CD45+,CD3+, CDS+; β-lymphocytes are indicated by CD45+, CD19+ or CD45+, CD20+; thrombocytes are indicated by CD45+, CD61+; and natural killer cells are indicated by CD16+, CD56+, and CD3−. Furthermore, two commonly used CD molecules, namely, CD4 and CD8, are, in general, used as markers for helper and cytotoxic T cells, respectively. These molecules are defined in combination with CD3+, as some other leukocytes also express these CD molecules (some macrophages express low levels of CD4; dendritic cells express high levels of CDS).

In other cases the rare cell is a pathogen, which includes, but is not limited to, gram-positive bacteria (e.g., *Enterococcus* sp. Group B *streptococcus*, Coagulase-negative *staphylococcus* sp. *Streptococcus viridans, Staphylococcus aureus* and saprophyicus, *Lactobacillus* and resistant strains thereof, for example); yeasts including, but not limited to *Candida albicans*, for example; gram-negative bacteria such as, but not limited to, *Escherichia coli, Klebsiella pneumoniae, Citrobacter koseri, Citrobacter freundii, Klebsiella oxytoca, Morganella morganii, Pseudomonas aeruginosa,*

*Proteus mirabilis, Serratia marcescens*, and Diphtheroids (gnb) and resistant strains thereof, for example; viruses such as, but not limited to, HIV, HPV, Flu, and MERSA, for example; and sexually transmitted diseases. In the case of detecting rare cell pathogens, a particle reagent is added that comprises a binding partner, which binds to the rare cell pathogen population. Additionally, for each population of cellular target rare molecules on the pathogen, a reagent is added that comprises a binding partner for the cellular target rare molecule, which binds to the cellular target rare molecules in the population.

The phrase "non-cellular target rare molecules" refers to target rare molecules that are not bound to a cell and/or that freely circulate in a sample. Such non-cellular target rare molecules include biomolecules useful in medical diagnosis of diseases, which include, but are not limited to, biomarkers for detection of cancer, cardiac damage, cardiovascular disease, neurological disease, hcmostasis/hcmastasis, fetal maternal assessment, fertility, bone status, hormone levels, vitamins, allergies, autoimmune diseases, hypertension, kidney disease, diabetes, liver diseases, infectious diseases and other biomolecules useful in medical diagnosis of diseases, for example.

The "MS label precursor" is any molecule that results in an MS label by the action of the alteration agent. The MS label precursor may itself be an MS label that, through the action of the alteration agent is converted to another MS label by cleavage, by reaction with a moiety, by derivatization, or by addition or by subtraction of molecules, charges or atoms, for example, or a combination of two or more of the above. The MS label precursor includes the label binding unit and the mass label.

The "mass label" label includes the "charge unit" and the "mass unit".

Figure 2:
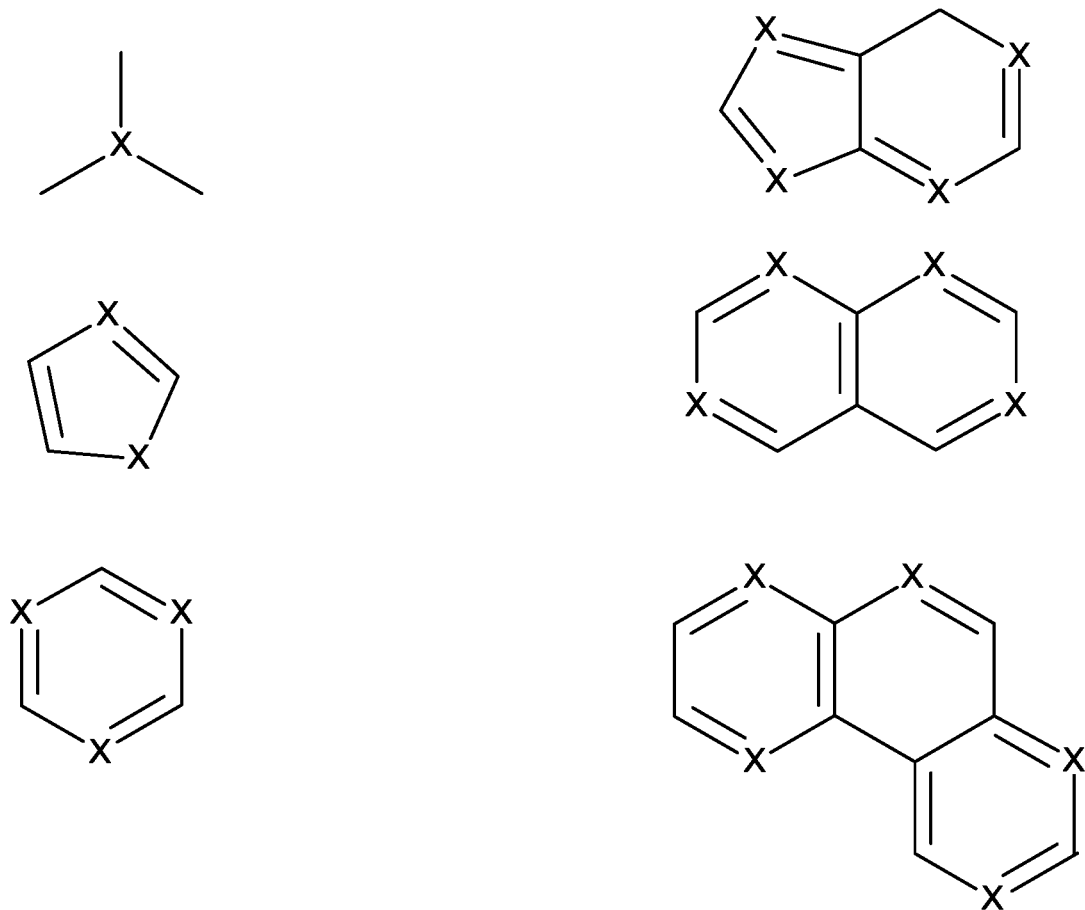
FIG. 2 is the charge unit where at least one X that is an N-R moiety such as a quaternary ammonium cation or where at least one X that is an quaternary phosphonium cation where X=P-R and where R can be an hydrogen, alkyl or aromatic organic derivatives such as methyl, benzyl or phenyl.
Figure 3A:
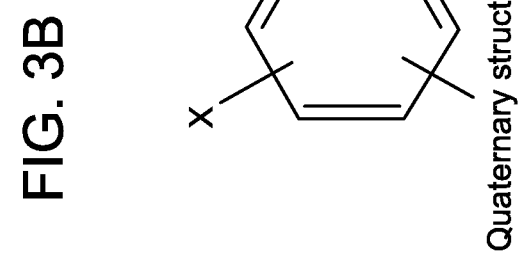
FIG. 3 panels A-D show a variable mass unit represented by Y that comprises at least one atom such as CH, $CH_2$, O, N, S, P or a molecule having a mass below 3 kDA such as a phenyl group shown in panel B and panel D. The variable mass unit, Y and the charge unit, which are constituents of the mass label, are connected through an acetal or ketal bond to an affinity reagent or rare molecule, represented by $R_1$ as shown in panel A and panel B or through an imine bond as shown in panel C and panel D.
Figure 3B:
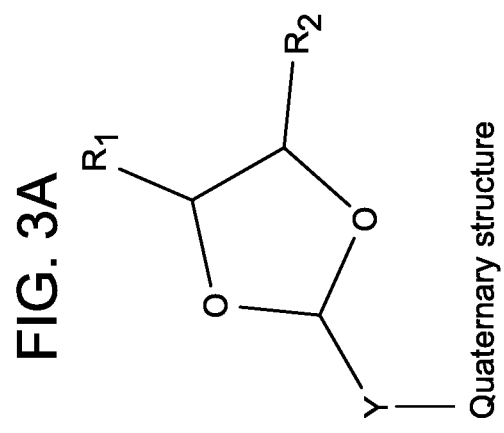
Figure 3C:
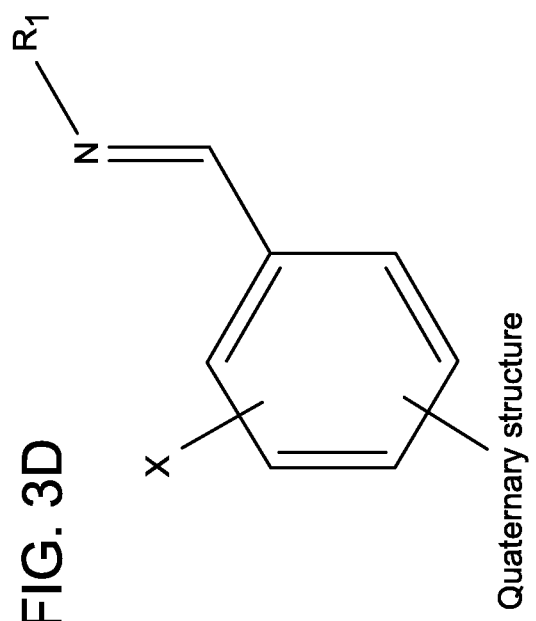
Figure 3D:
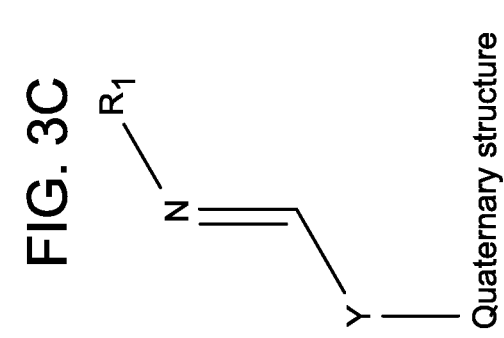

The "charge unit" comprises a group of atoms arranged in such a way that one of them bears a formal charge. The structures shown in FIG. 2 include at least one charge unit, X, which may be, for example, an N-R moiety such as a quaternary ammonium cation or at least one X is a quaternary phosphonium cation where X=P-R and where R can be an hydrogen, alkyl or aromatic organic derivatives such as methyl, benzyl or phenyl. Examples include carnitine, imidazolium, pyridinium, tetra ethyl amine, benzalkonium amine, alkyl benzethonium amine, triphenyl phosphonium cation trialkyl(2.3-dihydroxypropyl) phosphonium salts or other quaternary structures.

The term "mass unit" comprises at least one atom shown as Y in FIG. 3 such as CH. $CH_2$, O, N, S, P or a collection of atoms that have a combined mass below 3 kDA such as a phenyl group shown in 3a and 3b and is attached to the "charge unit". The variable mass unit can include structures of defined mass such as polypeptides, polymers, carboxylic acid, carbohydrates, cyclic rings, aromatic rings, hydrocarbon, organic amines, nucleic acids, and organic alcohols, for example, whose mass can be varied by substitution and chain size, for example. The "mass unit" can comprise additional molecules such as aromatic rings, peptides, fatty acids, carbohydrates, organic amines, nucleic acids, and organic alcohols, (e.g., alkyl alcohols, acyl alcohols, phenols, polyols (e.g., glycols), thiols, epoxides, primary, secondary and tertiary amines, indoles, tertiary and quaternary ammonium compounds, amino alcohols, amino thiols, phenolic amines, indole carboxylic acids, phenolic acids, vinylogous acid, carboxylic acid esters, phosphate esters, carboxylic acid amides, carboxylic acids from polyamides and polyesters, hydrazone, oxime, trimethylsilyl enol ether, carbamates, ureas, guanidines, isocyanates, sulfonic acids, sulfonamides, sulfonylureas, sulfates esters, monoglycerides, glycerol ethers, sphingosine which allows methods in accordance with the principles described herein to be multiplexed to obtain more than one result at a time.

Figure 4:
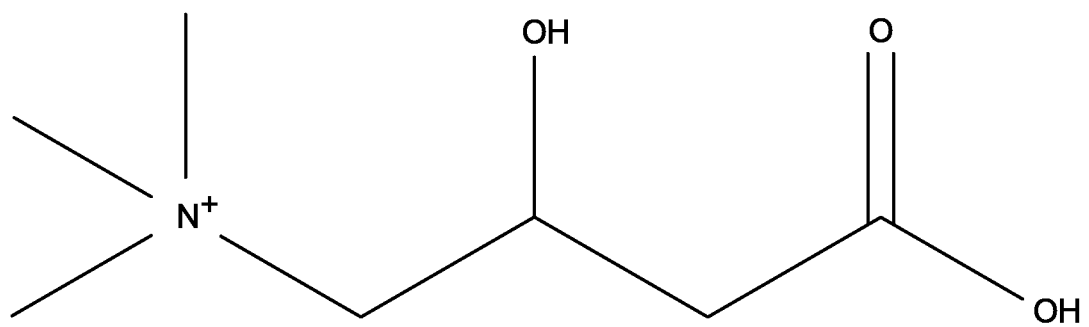
FIG. 4 is L-carnitine.
Figure 5:
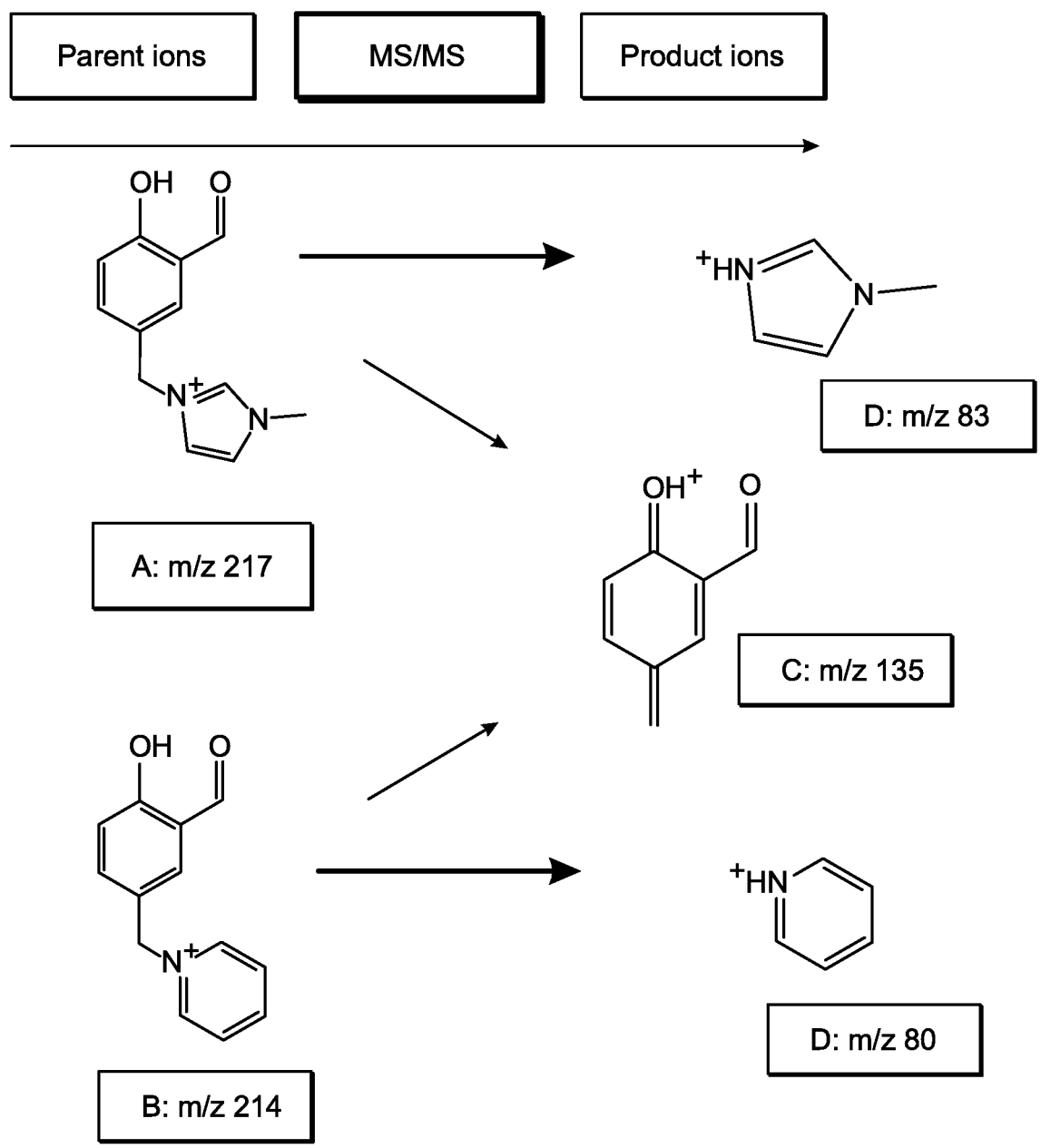
FIG. 5 shows mass labels with imidazolium (m/z 217) and pyridinium (m/z 214) structures as the charge unit as well as their respective product ions resulting from MS/MS. In this case, the variable mass unit is comprised of all other atoms in the molecule that do not directly connect to the pre-charged atom. The mass label generates unique fragment ions when they are subjected to MS/MS. For the imidazolium mass label, the unique fragment is observable at m/z 83 in the product ion MS/MS spectrum. For the pyridinium mass label, the unique fragment ion is observable at m/z 80 in the product ion MS/MS spectrum.

The "quaternary structure" and "mass structure" should be attach through a bond resistant to fragmentation such as a C—C, C—O, C—N or other covalent bond. For example, carnitine shown in FIG. 4 has a carboxylic acid to attach to the peptide mass labels, such as L-Cartinine-Phe-Ala-Gly-Gly-Ser-Cys, L-Cartinine-Phe-Thr-Ala-Ser-Ala-Cys, L-Cartinine-Phe-Phe-Ala-Ser-Cys, L-Cartinine-Phe-Phe-Ala-Ser-Cys L-cartinine-phe-gly-gly-ser-cys. L-cartinine-phe-phe-ser-gly-cys, L-cartinine-phe-gly-thr-thr-cys, L-cartinine-phe-gly-thr-ala-cys, Carnitine-arg-gly-cys and Carnitine-phe-cys. In another example methylimidazolium and pyridinium analogues of the quaternary mass label are connected to aromatic mass label through a —$CH_2$— bond as shown in FIG. 5.

Figure 6:
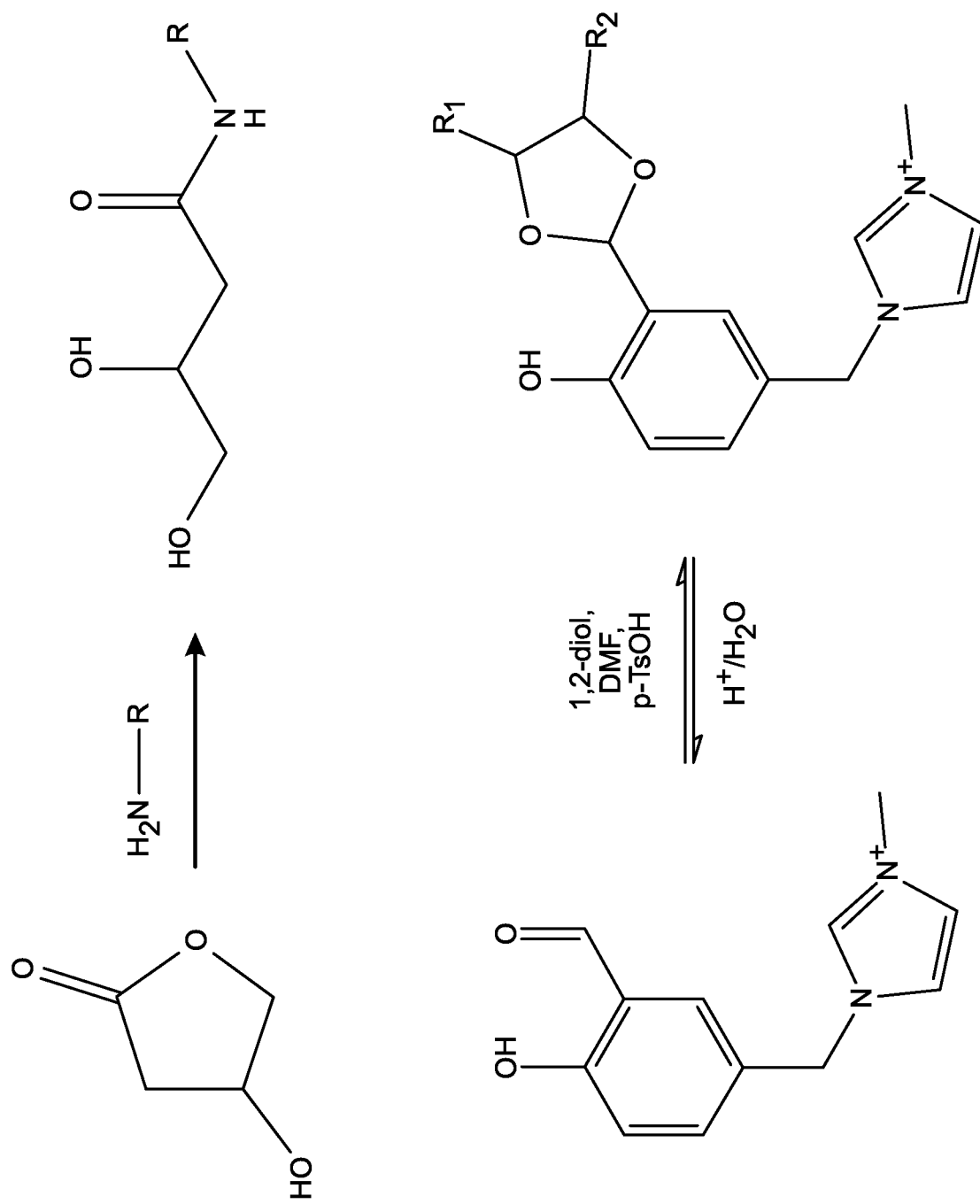
FIG. 6 shows how an affinity reagent or raw molecule represented by R is connected through an acetal or ketal bond to the quaternary mass label by reaction on a diol to an aldehyde on the mass structure Y. A diol is first attached to the amine of the affinity reagent or rare molecule by reaction of beta-hydroxy-gamma-butyrolactone to form an amide bond.

The mass labels are able to be attached to an affinity reagent or rare molecule with a label binding unit that facilitates reversible bond formation such as, for example, an acetal or ketal bond as shown in FIG. 3 panels A-D. FIG. 6 shows how an affinity reagent or rare molecule represented by R is connected through acetal or ketal bond the quaternary mass label. The label binding unit in this case is a diol which is produced by modification of an amine. This modification can be carried out by reaction of an amine with β-hydroxy-γ-butyrolactone. Other reversible linking chemistries are known in the art and suitable with the compositions of the invention, such as those described for example in U.S. patent application publication numbers 2011/0294952 and 2016/0086781, the contents of each of which is incorporated by reference herein in its entirety.

These acetal or ketal bonds are broken by hydrolysis upon exposure aqueous acid, which is termed the release reagent in this case. For example, a solvent of acetonitrile or water with acid will break the acetal or ketal bond and liberate the mass labels for analysis. It is important that the acetal or ketal bonds are not broken prematurely by exposure to liquids used for the affinity reactions and are stable during storage. In general, the bond between the label binding unit and the mass label may be broken with any suitable release reagent which, for example, may be heat, sonication or a chemical reagent such as an acid depending on whichever is suitable. Release reagents also include, but are not limited to, chemical agents such as, but not limited to, acids, catalysts (e.g., enzymes (including pseudoenzymes) and metals), oxidizing agents, reducing agents, acids, bases or other agents that promote the breakage of the acetal or ketal bond.

One or more mass labels can be attached to a single affinity reagent, such as any number from one to 3000 mass labels for any single affinity reagent. An advantage of having more than one mass label bound to a single affinity unit is the ability to produce signal amplification. Mainly, such an approach amplifies the signal because a number of individual molecules are generated that are measured by MS, which multiplies the signal by the number of individual molecules generated. That may be important in rare event detection in which the target may only be present as less than 1% of the sample.

Figure 7:
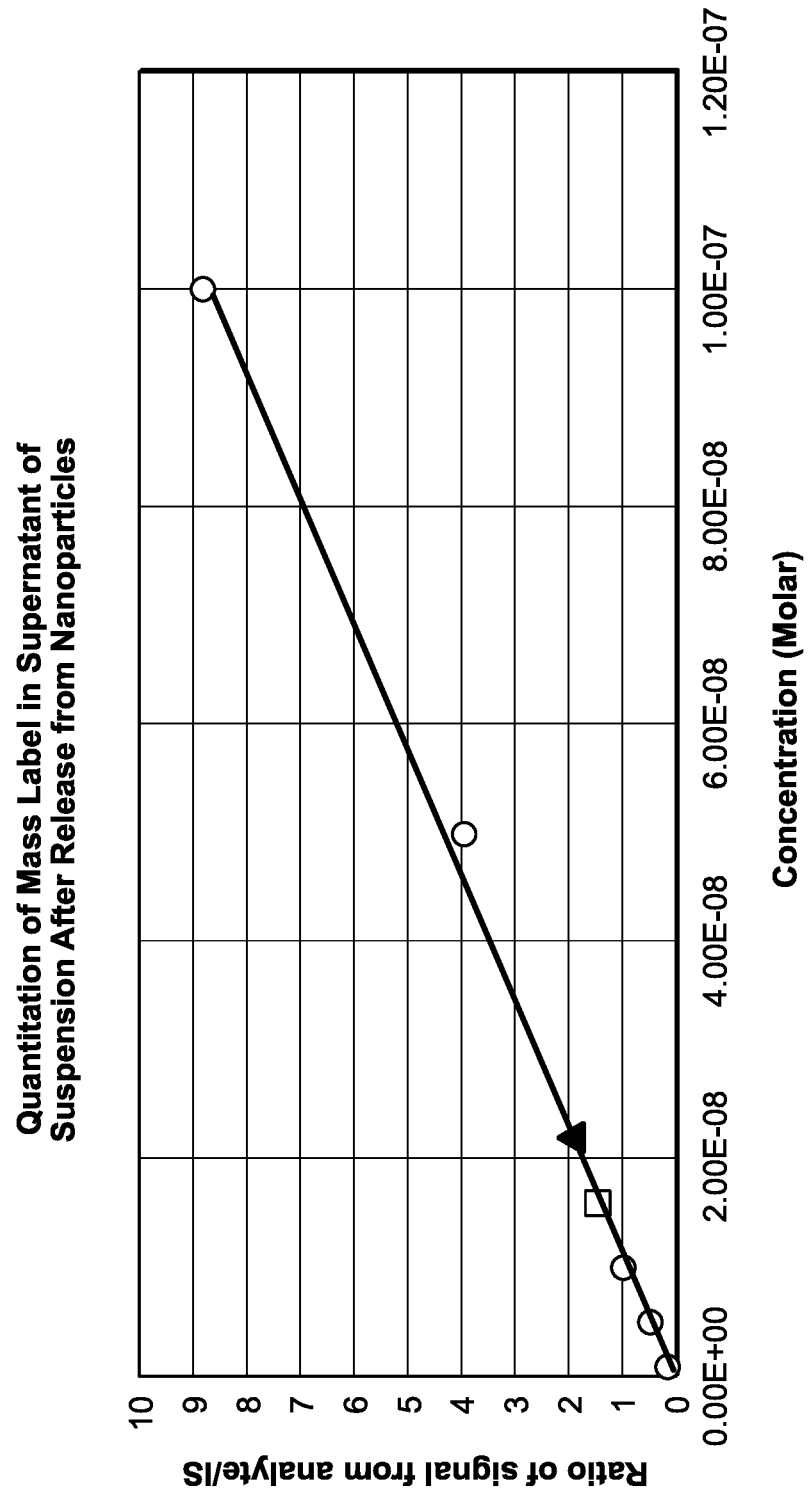
FIG. 7 shows the concentration of the mass label released into the release solution using a calibration curve. The sample (triangle) was diluted by four orders of magnitude. The supernatant from the final wash before release (square) was analyzed after a dilution of two orders of magnitude.

The quaternary mass label generates at a unique mass fragment due fragmentation upon ionization into a least one predictable mass, analytically separated from the background. The mass labels and their product ions are detected in the inside the mass spectrometer. FIG. 5 shows respective fragmentation pathways for methylimidazolium and pyridinium. FIG. 7 shows fragmentation pathways for higher molecular weight derivatives. The molecular weights of quaternary mass label are adjust such that the unique mass fragment is not in an region overlapping the masses of background components. FIG. 5 shows that quaternary mass labels with methylimidazolium (m/z 217) and pyridinium (m/z 214) as quaternary structures and aromatic mass structure (m/z 135). The quaternary mass label generates a unique mass fragment due fragmentation upon collision induced dissociation shown which are represented by methylimidazolium (m/z. 83) and pyridinium (m/z. 80). FIG. 7 shows that quaternary mass labels with high molecular weight derivatives of imidazolium (m/z 309 and m/z 259). These quaternary mass labels generate higher mass fragments due fragmentation upon ionization (m/z 175 and m/z 125).

The predictability of the fragmentation of the precursor mass label into one or more fragments (product ions) will depend on the chemical structure of the mass label. For carbon based mass labels, the predictability follows certain rules. For example, there is an order of stability of carbocations: primary<secondary<tertiary, with primary ions being less stable than secondary ones which in turn are less stable than tertiary ones. Applying the logic of this to fragmentation patterns, it means that a split which produces a secondary carbocation is going to be more successful than one producing a primary one. A split producing a tertiary carbocation will be more successful still. Ions with the positive charge on the carbon of a carbonyl group.

C=O, are also relatively stable.

Typically, a structure will be analyzes using the following conventions. Most fragments are even-electron cations. These split to make more even-electron cations. The probability of cleaving a given bond is related to the bond strength, and to the stability of the fragments formed. Ten general rules to keep in mind when predicting the most likely ions to be formed for a given molecule are as follows.

1) The relative height of the M+ peak is greatest for straight-chain molecules and decreases as the branching increases.
2) The relative height of the M+ peak decreases with chain length for a homologous series.
3) Cleavage is favored at alkyl-substituted carbons, with the probability of cleavage increasing as the substitution increases.

These rules mostly arise from the fact that carbocation and radical stability show the following trend: (Most Stable) Benzylic>Allylic>Tertiary>Secondary>>Primary (Least Stable "Stevenson's Rule"). At the point of breakage, the larger fragment usually takes the radical to leave the smaller cation.

4) Double bonds, cyclic structures, and especially aromatic rings will stabilize the molecular ion and increase its probability of appearance.
5) Double bonds favor allylic cleavage to give a resonance stabilized allylic carbocation, especially for cycloalkenes.

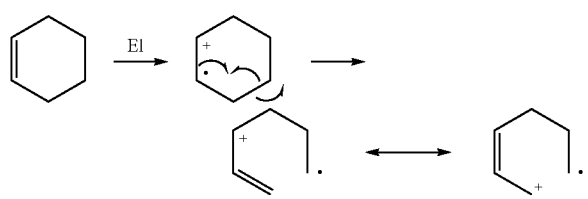

6) For saturated rings (like cyclohexanes), the side chains tend to cleave first leaving the positive charge with the ring.

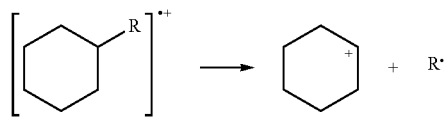

7) Unsaturated rings can also undergo retro-Diels-Alder reactions to eliminate a neutral alkene.

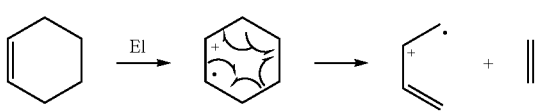

8) Aromatic compounds tend to cleave to give benzylic cations, or more likely tropylium cations.

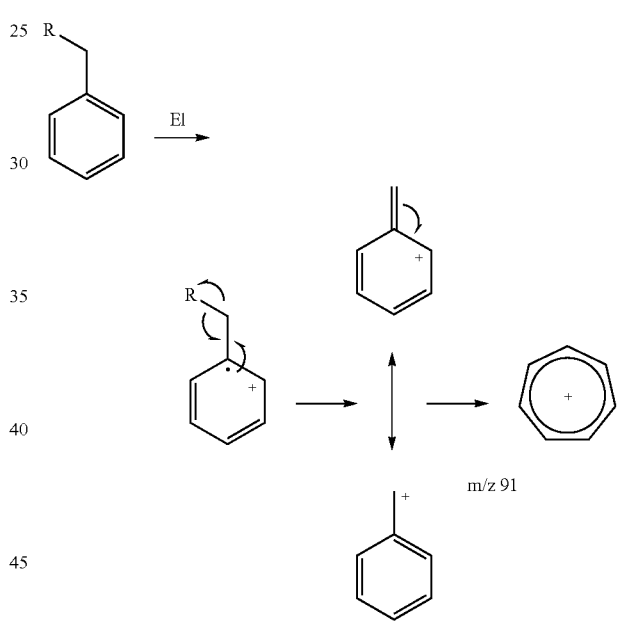

9) C—C bonds next to heteroatoms often break leaving the positive charge on the carbon with the heteroatom.

10) Cleavage is often favored if it can expel small stable molecules like water, CO, NH3, H2S, etc.

In addition to bond fragmentation, various intramolecular rearrangements can take place to give sometimes unexpected ions. One common type of rearrangement in MS is the McLafferty rearrangement which takes place in compounds that contain a carbonyl group.

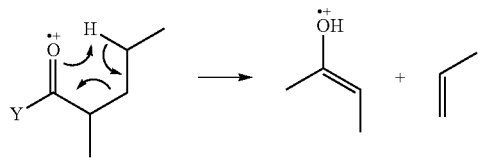

General rules 1-3 apply well to hydrocarbons. Rearrangements are common but usually do not give intense peaks. The fragmentation pattern may be characterized by peaks separated by 14 mass units (a $CH_2$ group). The most intense peaks are the C3-C5 fragments. The MS for branched saturated hydrocarbons are similar, except certain fragments become more prominent. Cyclic hydrocarbons show a much more intense M+ ion (Rule 4) Two bonds must break to form fragments. It is usually easy to see the M+ peak of alkenes. In acyclic alkenes, the double bond freely migrates in the fragments, so it can be difficult to determine the double bond location, but for cyclic alkenes it is easier. Cleavage usually happens at allylic bonds (Rule 5). Aromatic hydrocarbons usually show strong M+ peaks (Rule 4). Aromatic rings are stable and have a lower tendency to fragment. Alkyl substituted benzenes often give a strong peak at m/z 91 due to benzylic cleavage (Rule 8).

Alcohols fragment very easily—secondary and primary alcohols show very weak M+ peaks, and tertiary alcohols often do not show M+ at all. MW is often determined by derivatization. The C—C bond nearest the OH is frequently the first bond to break. Thus primary alcohols often show a prominent peak at 31 m/z. Secondary alcohols cleave in the same way, often showing a prominent $^+$CHR—OH peak. Sometimes the hydrogen $R_2$CH—OH in 1° and 2° alcohols cleaves rather than an alkyl group. The result is an M-1 peak. Tertiary alcohols cleave in a similar fashion to give $^+$CRR—OH fragments. Alcohols can lose a molecule of water to show a sometimes prominent M-18 peak. It is especially noticeable for primary alcohols. Benzylic alcohols fragment much differently from aliphatic alcohols. Benzylic cleavage happens as expected (Rule 8). Benzylic alcohols will usually lose water (M-18). The M-18 peak is especially strong for molecules for which loss of water is mechanistically straightforward. Phenols often show peaks at 77 m/z resulting from formation of phenyl cation, and peaks resulting from loss of CO (M-28) and CHO (M-29) are usually found in phenols. If alternative attractive cleavage pathways are available.

For ethers, cleavage happens in two main ways: breakage of the C—C bond next to O (like alcohols); or C—O bond cleavage with the charge on the C fragment. For aromatic ethers, M+ is usually strong. MS is similar to phenols—both form phenoxyl cation (m/z 93) and associated daughters.

Ketones usually give strong M+ peaks. A major fragmentation pathway involves α-cleavage to give an acylium ion. The carbonyl-containing fragment can also take the radical. For ketones with longer chains, the McLafferty rearrangement often leads to strong peaks. For aromatic ketones, M+ is evident. Primary cleavage is a to the carbonyl to give a strong ArCO+ peak (m/z 105 when Ar=Ph). This will lose CO to give the phenyl cation (m/z 77).

Aldehydes show weak but discernable M+ peaks. Major pathways are α-cleavage and McLafferty Rearrangement. Aromatic aldehydes are similar to aromatic ketones. M+ is strong, and M-1 (a—cleavage to carbonyl) is also strong to give the ArCO+ ion (m/z 105 for Ar=Ph). Loss of CO from this ion is common to give m/z77 phenyl cation.

For carboxylic acids, M+ is weak, and not always visible. A characteristic m/z 60 peak is often present due to the McLafferty Rearrangement. Bonds a to carbonyl also frequently break to give M—OH and M—$CO_2$H peaks.

For aromatic acids, M+ is very prominent. Common peaks are loss of OH (M-17) and loss of $CO_2$H (M-45). If an ortho hydrogen-bearing group is present, loss of water (M-18) is visible as well.

For aliphatic esters. M+ is usually distinct. The most characteristic peak is due to the McLafferty rearrangement. M+ is usually prominent, unless RO chain is long. The base peak is loss of RO•. The McLafferty rearrangement give the corresponding acid. A more complicated rearrangement often gives a prominent acid+1 peak.

Aliphatic monoamines have odd numbered and weak M+ peaks. Most important cleavage is usually breakage of the C—C bond next to the C—N bond. The base peak in nearly all primary amines comes at 30 m/z. For aromatic amines, M+ is intense. An NH bond can be broken to give a moderately intense M-1 peak. A common fragmentation is loss of HCN and H2CN to give peaks at 65 and 66 m/z. Alkyl substituted aromatic amines typically show breakage of the C—C bond next to the C—N to give a strong peak at 106 when Ar=Ph.

Primary amides give a strong peak at m/z 44 due to breakage of the R—$CONH_2$ bond. Aliphatic amides—M+ is weak but discernible. For straight-chain amides more than 3 carbons, McLafferty gives the base peak at m/z 59.

For nitriles. M+ are weak or absent for aliphatic nitriles. Loss of the α—hydrogen can give a weak M-1 peak. Base peak is usually 41 due to a rearrangement like the McLafferty. This has limited diagnostic value since (C3H5+) has the same mass.

Aliphatic nitro compounds have weak odd M+. The main peaks are hydrocarbon fragments up to M—$NO_2$. For aromatic nitro compounds, M+ is strong. Prominent peaks result from loss of $NO_2$ radical to give an M-46 peak. Also prominent is M-30 from loss of NO.

Figure 9:
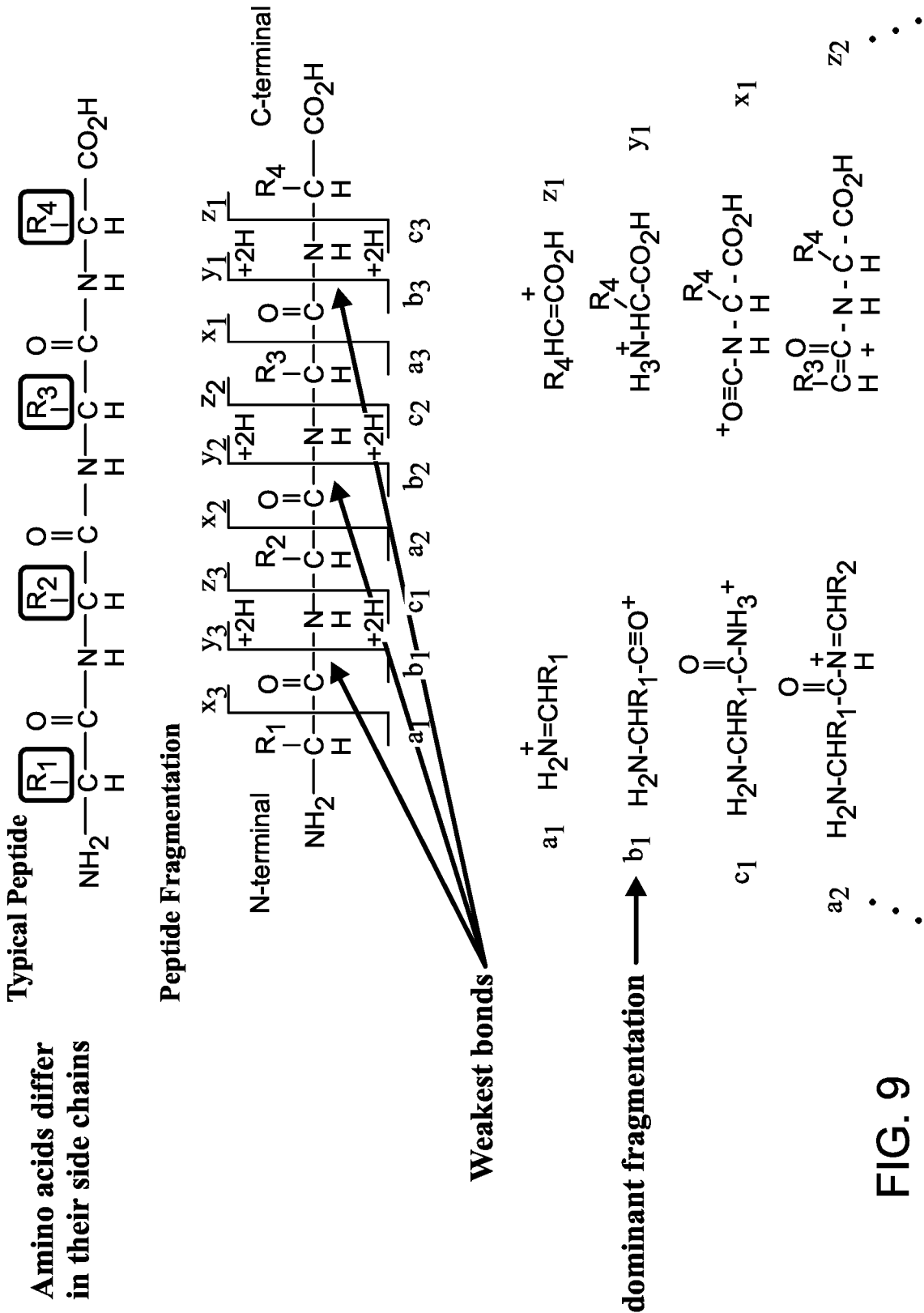
FIG. 9 describes a process for predicting fragmentation of a peptide mass label in a mass spectrometer.

FIG. 9 describes a process for predicting fragmentation of a peptide mass label in a mass spectrometer. Fragmentation of peptides (amino acid chains) typically occurs along the peptide backbone. Each residue of the peptide chain successively fragments off, both in the N->C and C->N direction. Amino acids differ in their side chains. As shown in FIG. 9, each amino acid has a weakest bond based on the different side chains which results in predictable fragmentation of the peptide. Peptides have a tendency to fragment at Asp (D) (Mass Spectrometry in Proteomics Ruedi Acbersold* and David R. Goodlett 269 Chem. Rev. 2001, 101, 269-295). Predicting the fragmentation of a peptide in a mass spectrometer is further described for example in Beardsley et al. (Journal of the American Society for Mass Spectrometry, 15(2): 158-167, 2004), the content of which is incorporated by reference herein in its entirety. Peptide fragmentation algorithms are also commercially available. An exemplary algorithm for predicting peptide fragmentation is described by Zhang (Analytical Chemistry 76, 3908-3922, 2004) or Zhang (Analytical Chemistry 77, 6364-6373, 2005), the content of each of which is incorporated by reference herein in its entirety.

In certain embodiments, the peptide is labeled, at the N terminal, C terminal, or any internal amino acid residue. For example, commercially available small cysteine terminated peptides (e.g. YGMTSR*YFC, where the arginine is fully labeled with 13C6 and 14N4) may be selected as the mass label.

The term "alteration agent" or "releasing agent" refers to a substance that has the ability to alter the MS label precursor, breaking the bond of the label binding unit to release the mass label. In certain embodiments, the alteration agent is able to interact with the MS label precursor to achieve an MS label having a unique mass in the range of about 1 Da to about 3 kDa, or in the range of about 1 Da to about 50 Da, or in the range of about 50 Da, to about 150 Da, or in the range of about 150 Da to about 700 Da, or in the range of about 700 Da to about 3 kDa. In some examples the unique mass of the MS label is below about 3 kDa. The MS label precursor can be altered by bond breaking to form a neutral, negative or positive ion, or radical. The alteration of the MS label precursor by the alteration agent may be by addition of atoms, charges or electrons to, or subtraction of atoms, charges or electrons from the MS label precursor or by bond cleavage in, or bond formation in, the MS label precursor. The alteration agents include, but are not limited to, chemical agents such as, but not limited to, catalysts (e.g., enzymes (including pseudoenzymes) and metals), oxidizing agents, reducing agents, acids, bases, agents that promote substitution reactions or replacement reactions; and ionization agents. In some examples, the alteration agent facilitates the formation of an MS label from the MS label precursor by promoting the reaction of the MS label precursor with a moiety to form the MS label, for example. In some examples the alteration agent facilitates the formation of an MS label from the MS label precursor by promoting the release of the MS label from the MS label precursor, for example.

The nature of the MS label precursors may be dependent for example on one or more of the nature of the MS label, the nature of the MS method employed, the nature of the MS detector employed, the nature of the target rare molecules, the nature of the affinity agent, the nature of any immunoassay employed, the nature of the sample, the nature of any buffer employed, the nature of the separation. In some examples, the MS label precursors are molecules whose mass can be varied by substitution and/or chain size. The MS labels produced from the MS label precursors are molecules of defined mass, which should not be present in the sample to be analyzed. Furthermore, the MS labels should be in the range detected by the MS detector, should not have overlapping masses and should be detectable by primary mass. Examples, by way of illustration and not limitation, of MS label precursors for use in methods of the invention include, by way of illustration and not limitation, polypeptides, organic and inorganic polymers, fatty acids, carbohydrates, cyclic hydrocarbons, aliphatic hydrocarbons, aromatic hydrocarbons, organic carboxylic acids, organic amines, nucleic acids, organic alcohols (e.g., alkyl alcohols, acyl alcohols, phenols, polyols (e.g., glycols), thiols, epoxides, primary, secondary and tertiary amines, indoles, tertiary and quaternary ammonium compounds, amino alcohols, amino thiols, phenolic amines, indole carboxylic acids, phenolic acids, vinylogous acid, carboxylic acid esters, phosphate esters, carboxylic acid amides, carboxylic acids from polyamides and polyesters, hydrazone, oxime, trimethylsilyl enol ether, acetal, ketal, carbamates, ureas, guanidines, isocyanates, sulfonic acids, sulfonamides, sulfonylureas, sulfates esters, monoglycerides, glycerol ethers, sphingosine bases, ceramines, cerebrosides, steroids, prostaglandins, carbohydrates, nucleosides and therapeutic drugs.

An MS label precursor can include 1 to about 100.000 MS labels, or about 10 to about 100,000 MS labels, or about 100 to about 100,000 MS labels, or about 1,000 to about 100,000 MS labels, or about 10,000 to about 100,000 MS labels. The MS label precursor can be comprised of proteins, polypeptides, polymers, particles, carbohydrates, nucleic acids, lipids or other macromolecules capable of including multiple repeating units of MS labels by attachment. Multiple MS labels allow amplification as every MS label precursor can generate many MS labels.

With polypeptide MS label precursors, for example, the chain length of the polypeptide can be adjusted to yield an MS label in a mass region without background peaks. Furthermore, MS labels may be produced from the MS label precursors having unique masses, which are not present in the sample tested. The polypeptide MS label precursors can comprise additional amino acids or derivatized amino acids, which allows methods to be multiplexed to obtain more than one result at a time. Examples of polypeptide MS label precursors include, but are not limited to, polyglycine, polyalanine, polyserine, polythreonine, polycysteine, polyvaline, polylcucine, polyisoleucine, polymethionine, polyproline, polyphenylalanine, polytyrosine, polytryptophan, polyaspartic acid, polyglutamic acid, polyasparagine, polyglutamine, polyhistidine, polylysine and polyarginine, for example. Polypeptide MS label precursors differentiated by mixtures of amino acids or derivatized amino acids generate masses having even or odd election ion with or without radicals. In some examples, polypeptides are able to be modified by catalysis. For example, by way of illustration and not limitation, phenol and aromatic amines can be added to polythreonine using a peroxidase enzyme as a catalyst. In another example, by way of illustration and not limitation, electrons can be transferred to aromatic amines using peroxidase enzyme as a catalyst. In another example, by way of illustration and not limitation, phosphates can be removed from organic phosphates using phosphatases as a catalyst.

In another example, by way of illustration and not limitation, a derivatization agent is employed as a moiety to generate an MS label from an MS label precursor. For example, dinitrophenyl and other nitrophenyl derivatives may be formed from the MS label precursor. Other examples include, by way of illustration and not limitation, esterification, acylation, silylation, protective alkylation, derivatization by ketone-base condensations such as Schiff bases, cyclization, formation of fluorescent derivatives, and inorganic anions. The derivatization reactions can occur in microreaction prior to MS analysis but after affinity reaction or be used to generate MS label precursors conjugated to affinity reagents.

In some examples, the MS label precursor can comprise an isotope such as, but not limited to, $^2$H, $^{13}$C, and $^{18}$O, for example, which remains in the MS label that is derived from the MS label precursor. The MS label can be detected by the primary mass or a secondary mass after ionization. In some examples, the MS label precursor is one that has a relatively high potential to cause a bond cleavage such as, but not limited to, alkylated amines, acetals, primary amines and amides, for example, where the MS label can generate a mass that has even or odd election ion with or without radicals. Selection of the polypeptide can generate a unique MS spectral signature.

As mentioned above, the alteration agent may be an enzyme (which includes pseudoenzymes). In some examples, catalysis can occur with water insoluble enzyme derivatives immobilized with, for example, silica gels, charcoals, DEAE-cellulose, DEAE-SEPHADEX (cross-linked dextran gel, commercially available from Sigma Aldrich), cellulose citrate, kaolinite, cellulose phosphate, acid clay.

AMBERLITE XE-97 (carboxylic cation exchange resin manufactured by Rohm & Haas), carboxymethyl cellulose, glass, quartz, dowex-50, starch gel, polyacrylamide gel, poly amino acids, or aminobenzyl cellulose. Cross-linking agents can be used to immobilize the enzyme. Such cross-linking agents include, but are not limited to, glutaraldehyde, dimethyl adipimidate, carbodiimide, maleic anhydride, MDA methylenedianiline, hydrazide, and acyl azides, for example.

In some examples, an enzyme for purposes in accordance with the principles described herein is any enzyme with a high turnover rate that can convert as an enzyme substrate (such as an MS label precursor) into an MS label that is detected by the mass detector of a mass spectrometer in the presence of the un-converted substrate. The enzyme should not be in the sample tested or, if present in the sample, it must be removed from the sample prior to testing. Examples of enzymes suitable for this purpose include, but are not limited to, phosphatases (e.g., alkaline phosphatase, lipid phosphatases, tyrosine phosphatase, serine phosphatase, threonine phosphatase, and histidine phosphatase); oxidases (e.g., horse radish peroxidase, copper amine oxidase, D-amino acid oxidase, galactose oxidase, plasma amine oxidase, tryptophan peroxidase, uricase oxidase, and xanthine oxidase); β-galactosidase; transferases (e.g., D-alanine transferase, glycosyl transferase, acyl transferase, alkyl transferase, aryl transferase, single carbon transferase, ketone transferase, aldehyde transferase, nitrogenous transferase, phosphorus transferase, sulfur transferase, and pentosyl transferase); peptidases (e.g., pepsin, papain, rennin (chymosin), renin, thrombin, trypsin, matrix metallopeptidase, cathespin, cysteine protease, and carboxypeptidase); aldolases (e.g., carboxyl aldolase, aldehyde aldolase, oxo acids, tryptophanase); fatty acid enzymes (e.g., fatty acid amine hydrolase, fatty acid synthase, and choline acetyltransferase), for example, and combinations of two or more of the above (e.g., two or more of alkaline phosphatase, acid phosphatase, an oxidase, ß-galactosidase, peroxidase, acylase, asparaginase, catalase, chymotrypsin, amylase, glucoamylase, glucose oxidase, glucose-6-phosphate dehydrogenase, hexokinase, invertase, lipase, phosphoglucomutase, ribonuclease, acetylcholinesterase, alcohol dehydrogenase, aldolase, cholinesterase, citrate synthetase, urease, amylglucosidase, carboxypeptidase, cholinesterase, luciferase, ribonuclease, pyruvate kinase, and subtilopeptidase).

Substrates for the enzymes are MS label precursors that comprise an MS label that is released by the action of the enzyme on the substrate. Such MS labels that may be part of an enzyme substrate include, by way of illustration and not limitation, phenols (from substrates such as, for example, p-nitrophenyl phosphate, p-nitrophenyl-β-D-galactoside, amino acids, peptides, carbohydrates (6-phospho-D-gluconate), fatty acids (acetyl-CoA), alkyl amines, glycerols); and naphthols (from substrates such as, for example, p-nitronaphthyl phosphate, p-nitro-naphthyl-β-D-galactoside); for example.

Metals that may be employed to release an MS label from a moiety attached to an affinity agent include, but are not limited to, transition metals (e.g., palladium, platinum, gold, ruthenium, rhodium, or iridium), chelated metals (e.g., iron, copper, cobalt, magnesium complexed by ethylenediaminetetraacetate (EDTA), N-(2-hydroxyethyl)-ethylenediaminetriacetic acid (HEDTA), or trans-1,2-cyclohexanediaminetetraacetic acid (CDTA), for example), metal oxidants (e.g., sodium hypochlorite, potassium periodate, silver oxide, chromic acid, potassium permanganate, and sodium perborate) and metal reductants (e.g., lithium aluminum hydride, sodium borohydride, sodium ascorbate, phosphites, and sodium), for example.

The MS label can be detected directly or the released MS label can be further reacted with another compound to form a derivative MS label, which is detected by MS techniques. A derivative MS label is a compound that is formed from an MS label that is obtained from the MS label precursor where the compound also is detectable by MS techniques. This approach of forming a derivate MS label further enhances the multiplexing capability of methods in accordance with the principles described herein. For example, a released phenol or naphthol can couple to an aromatic amine in the presence of a peroxidase (see, for example, U.S. Pat. No. 5,182,213, the relevant disclosure of which is incorporated herein by reference). In one example, a released naphthol is coupled with a phenylenediamine such as, for example, α-phenylenediamine dihydrochloride, in the presence of a peroxidatively active substance in an alkaline medium to produce a derivative MS label. Multiplexing may be achieved using different naphthols and/or different phenylenediamines.

Internal standards are an important aspect of mass spectral analysis. In some examples, a second mass label can be added that can be measured (as an internal standard) in addition to the MS label used for detection of the rare target molecule. The internal standard has a similar structure to the MS label with a slight shift in mass. The internal standards can be prepared that comprise additional amino acids or derivatized amino acids. Alternatively, the internal standard can be prepared by incorporating an isotopic label such as, but not limited to 2H (D), 13C, and 18O), for example. The MS isotope label has a mass higher than the naturally-occurring substance. For example, the isotope labeled MS labels, for example, glycerol-C-d7, sodium acetate-C-d7, sodium pyruvate-C-d7, D-glucose-C-d7, deuterated glucose, and dextrose-C-d7, would serve as internal standards for glycerol, sodium acetate, sodium pyruvate, glucose and dextrose, respectively.

An MS label precursor or an alteration agent may be attached to an affinity agent (to yield a modified affinity agent) covalently either directly by a bond or through the intermediacy of a linking group. In some embodiments, the preparation of a modified affinity agent may be carried out by employing functional groups suitable for attaching the MS label precursor or the alteration agent, to the affinity agent by a direct bond. The nature of the functional groups employed is dependent, for example, on one or more of the nature of the MS label precursor, the nature of the alteration agent, and the nature of the affinity agent including the nature of one or more different particles such as, e.g., carrier particles and label particles that may be part of the affinity agent. A large number of suitable functional groups are available for attaching to amino groups and alcohols; such functional groups include, for example, activated esters including, e.g., carboxylic esters, imidic esters, sulfonic esters and phosphate esters; activated nitriles; aldehydes; ketones; and alkylating agents.

The linking group may be a chain of from 1 to about 60 or more atoms, or from 1 to about 50 atoms, or from 1 to about 40 atoms, or from 1 to 30 atoms, or from about 1 to about 20 atoms, or from about 1 to about 10 atoms, each independently selected from the group normally consisting of carbon, oxygen, sulfur, nitrogen, and phosphorous, usually carbon and oxygen. The number of heteroatoms in the linking group may range from about 0 to about 8, from about 1 to about 6, or about 2 to about 4. The atoms of the linking group may be substituted with atoms other than hydrogen such as, for example, one or more of carbon, oxygen and nitrogen in the form of, e.g., alkyl, aryl, aralkyl, hydroxyl, alkoxy, aryloxy, or aralkoxy groups. As a general rule, the length of a particular linking group can be selected arbitrarily to provide for convenience of synthesis with the proviso that there is minimal interference caused by the linking group with the ability of the linked molecules to perform their function related to the methods disclosed herein.

The linking group may be aliphatic or aromatic. When heteroatoms are present, oxygen will normally be present as oxy or oxo, bonded to carbon, sulfur, nitrogen or phosphorous; sulfur will be normally be present as thioether or thiono; nitrogen will normally be present as nitro, nitroso or amino, normally bonded to carbon, oxygen, sulfur or phosphorous; phosphorous will be normally bonded to carbon, sulfur, oxygen or nitrogen, usually as phosphonate and phosphate mono- or diester. Functionalities present in the linking group may include esters, thioesters, amides, thioamides, ethers, ureas, thioureas, guanidines, azo groups, thioethers, carboxylate and so forth. The linking group may also be a macro-molecule such as polysaccharides, peptides, proteins, nucleotides, and dendrimers.

In some embodiments the MS label precursor, or the alteration agent, as the case may be, and the affinity agent may be linked together non-covalently. Members of a binding pair, usually a specific binding pair, are employed where one member is linked to the affinity agent and the other member is linked to the MS label precursor or to the alteration agent. Binding of the binding pair members results in the non-covalent linking of the affinity agent and the MS label precursor or the alteration agent. The binding pair members may be linked directly to one or both of the MS label precursor, or the alteration agent, and the affinity agent or indirectly through the intermediacy of a linking group, the nature of which is discussed above. In some examples, the members of the specific binding pair have a relatively high binding constant such as, by way of illustration and not limitation, avidin (streptavidin)-biotin binding, fluorescein (FITC) and antibody for FITC, rhodamine (Texas red) and antibody for rhodamine, digitonin (DIG) and antibody for DIG, non-human species antibody (e.g., goat, rabbit, mouse, chicken, sheep) and anti-species antibody, for example.

The modified affinity agents can be prepared by linking each different affinity agent in separate, individual reactions to the MS label precursor or the alteration agent and then combining the modified affinity agents to form a mixture comprising the modified affinity agents. Alternatively, the different affinity agents can be combined and the reaction to link the affinity agents to the MS label precursor or the alteration agent can be carried out on the combination. This allows the method to be multiplexed for more than one result at a time.

An amount of each different modified affinity agent that is employed in the methods of the invention is dependent for example on one or more of the nature and potential amount of each different population of target rare molecules, the nature of the MS label, the nature of the affinity agent, the nature of a cell if present, the nature of a particle if employed, and the amount and nature of a blocking agent if employed. In some examples, the amount of each different modified affinity agent employed is about 0.001 µg/µL to about 100 µg/µL, or about 0.001 µg/µL to about 80 µg/µL, or about 0.001 µg/µL to about 60 µg/µL, or about 0.001 µg/µL to about 40 µg/µL, or about 0.001 µg/µL to about 20 µg/µL, or about 0.001 µg/µL to about 10 µg/µL, or about 0.5 µg/µL to about 100 µg/µL, or about 0.5 µg/µL to about 80 µg/µL, or about 0.5 µg/µL, to about 60 µg/µL, or about 0.5 µg/µL, to about 40 µg/µL, or about 0.5 µg/µL, to about 20 µg/µL, or about 0.5 µg/µL, to about 10 µg/µL.

The number of alteration agents employed may be one per MS label precursor, or one per two MS label precursors, or one per three MS label precursors up to one per all MS label precursors employed depending on one or more of the nature of the MS label precursor, the nature of the alteration agent, whether the alteration agent is free in the medium or part of a modified affinity agent, and the nature and number of different affinity reagents used. For example, where each of the MS label precursors include a labile ester or a labile amide linkage of different MS labels to the affinity agents, a single alteration agent may be employed that results in hydrolysis of the disulfide, ester or amide linkages to yield the different MS labels. In other examples utilizing one alteration agent, or fewer alteration agents than the number of MS label precursors, may be employed. In another example, a different alteration agent can be used to generate an MS label for each different type of affinity agent used.

The combination comprising the sample (optionally concentrated) and the modified affinity agents in the aqueous medium is treated by holding for a period of time and at a temperature for binding of the modified affinity agents to target rare molecules on the cells or on the particle reagents. For each modified affinity agent that comprises an alteration agent, an MS label precursor upon which the alteration agent acts is included in the combination wherein the MS label precursor is converted to the MS label. In some examples, an additional moiety is added where the alteration agent facilitates the reaction of the moiety with the MS label precursor to yield an MS label. In some examples, the modified affinity agent comprises an MS label precursor and the alteration agent is included in the combination as an unbound substance in the medium. In this example, the alteration agent acts upon the MS label precursor of the affinity agent to produce an MS label. In some examples, a first alteration agent is employed that releases an entity that comprises an MS label precursor from the affinity agent and a second alteration agent is subsequently employed to facilitate the formation of an MS label from an MS label precursor.

The temperature and duration of this treatment is dependent for example on the nature of the sample, the nature of the target rare molecules, the nature of the non-rare molecules, the nature of the modified affinity agents, the nature of the MS label precursors, and the nature of the alteration agents. In some examples, moderate temperatures are normally employed and usually constant temperature, preferably, room temperature. Temperatures during holding a period normally range from about 5° C., to about 99° C., or from about 15° ° C. to about 70° C., or about 20° C., to about 45° C., for example. The holding period is about 0.2 seconds to about 24 hours, or about 1 second to about 6 hours, or about 2 seconds to about 1 hour, or about 1 to about 15 minutes, for example. The time period depends on, for example, the temperature of the medium and the rate of binding of the various reagents.

Modified affinity agents, i.e., affinity agents that have been acted upon by an alteration agent, which have become bound to target rare molecules, optionally, are separated from modified affinity agents that have not become bound to target molecules. In some examples, this separation involves reducing the number of non-rare molecules in the sample.

Sample

The compositions of the invention can be used to analyze many different types of sample. A wide range of heterogeneous samples can be analyzed, such as biological samples, environmental samples (including, e.g., industrial samples and agricultural samples), and food/beverage product samples, etc.).

Exemplary environmental samples include, but are not limited to, groundwater, surface water, saturated soil water, unsaturated soil water; industrialized processes such as waste water, cooling water; chemicals used in a process, chemical reactions in an industrial processes, and other systems that would involve leachate from waste sites; waste and water injection processes; liquids in or leak detection around storage tanks; discharge water from industrial facilities, water treatment plants or facilities; drainage and leachates from agricultural lands, drainage from urban land uses such as surface, subsurface, and sewer systems; waters from waste treatment technologies; and drainage from mineral extraction or other processes that extract natural resources such as oil production and in situ energy production.

Additionally exemplary environmental samples include, but certainly are not limited to, agricultural samples such as crop samples, such as grain and forage products, such as soybeans, wheat, and corn. Often, data on the constituents of the products, such as moisture, protein, oil, starch, amino acids, extractable starch, density, test weight, digestibility, cell wall content, and any other constituents or properties that are of commercial value is desired.

Exemplary biological samples include a human tissue or bodily fluid and may be collected in any clinically acceptable manner. A tissue is a mass of connected cells and/or extracellular matrix material, e.g., skin tissue, hair, nails, nasal passage tissue, CNS tissue, neural tissue, eye tissue, liver tissue, kidney tissue, placental tissue, mammary gland tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sputum, sweat, amniotic fluid, menstrual fluid, mammary fluid, peritoneal fluid, urine, semen, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed.

In one embodiment, the biological sample can be a blood sample, from which plasma or serum can be extracted. The blood can be obtained by standard phlebotomy procedures and then separated. Typical separation methods for preparing a plasma sample include centrifugation of the blood sample. For example, immediately following blood draw, protease inhibitors and/or anticoagulants can be added to the blood sample. The tube is then cooled and centrifuged, and can subsequently be placed on ice. The resultant sample is separated into the following components: a clear solution of blood plasma in the upper phase; the buffy coat, which is a thin layer of leukocytes mixed with platelets; and erythrocytes (red blood cells). Typically, 8.5 mL of whole blood will yield about 2.5-3.0 mL of plasma.

Blood serum is prepared in a very similar fashion. Venous blood is collected, followed by mixing of protease inhibitors and coagulant with the blood by inversion. The blood is allowed to clot by standing tubes vertically at room temperature. The blood is then centrifuged, wherein the resultant supernatant is the designated serum. The serum sample should subsequently be placed on ice.

Prior to analyzing a sample, the sample may be purified, for example, using filtration or centrifugation. These techniques can be used, for example, to remove particulates and chemical interference. Various filtration media for removal of particles includes filer paper, such as cellulose and membrane filters, such as regenerated cellulose, cellulose acetate, nylon, PTFE, polypropylene, polyester, polyethersulfone, polycarbonate, and polyvinylpyrolidone. Various filtration media for removal of particulates and matrix interferences includes functionalized membranes, such as ion exchange membranes and affinity membranes; SPE cartridges such as silica- and polymer-based cartridges; and SPE (solid phase extraction) disks, such as PTFE- and fiberglass-based. Some of these filters can be provided in a disk format for loosely placing in filter holdings/housings, others are provided within a disposable tip that can be placed on, for example, standard blood collection tubes, and still others are provided in the form of an array with wells for receiving pipetted samples. Another type of filter includes spin filters. Spin filters consist of polypropylene centrifuge tubes with cellulose acetate filter membranes and are used in conjunction with centrifugation to remove particulates from samples, such as serum and plasma samples, typically diluted in aqueous buffers.

Filtration is affected in part, by porosity values, such that larger porosities filter out only the larger particulates and smaller porosities filtering out both smaller and larger porosities. Typical porosity values for sample filtration are the 0.20 and 0.45 µm porosities. Samples containing colloidal material or a large amount of fine particulates, considerable pressure may be required to force the liquid sample through the filter. Accordingly, for samples such as soil extracts or wastewater, a prefilter or depth filter bed (e.g. "2-in-1" filter) can be used and which is placed on top of the membrane to prevent plugging with samples containing these types of particulates.

In some cases, centrifugation without filters can be used to remove particulates, as is often done with urine samples. For example, the samples are centrifuged. The resultant supernatant is then removed and frozen.

After a sample has been obtained and purified, the sample can be analyzed with compositions of the invention to detect one or more target analytes, such as rare molecules within a blood plasma sample. With respect to the analysis of a blood plasma sample, there are many elements present in the plasma, such as proteins (e.g., Albumin), ions and metals (e.g., iron), vitamins. hormones, and other elements (e.g., bilirubin and uric acid). Any of these elements may be detected using compositions of the invention. More particularly, compositions of the invention can be used to detect molecules in a biological sample that are indicative of a disease state. Specific examples are provided below.

Where one or more of the target rare molecules are part of a cell, the aqueous medium may also comprise a lysing agent for lysing of cells. A lysing agent is a compound or mixture of compounds that disrupt the integrity of the membranes of cells thereby releasing intracellular contents of the cells. Examples of lysing agents include, but are not limited to, non-ionic detergents, anionic detergents, amphoteric detergents, low ionic strength aqueous solutions (hypotonic solutions), bacterial agents, aliphatic aldehydes, and antibodies that cause complement dependent lysis, for example. Various ancillary materials may be present in the dilution medium. All of the materials in the aqueous medium are present in a concentration or amount sufficient to achieve the desired effect or function.

In some examples, where one or more of the target rare molecules are part of a cell, it may be desirable to fix the cells of the sample. Fixation of the cells immobilizes the cells and preserves cell structure and maintains the cells in a condition that closely resembles the cells in an in vivo-like condition and one in which the antigens of interest are able to be recognized by a specific affinity agent. The amount of fixative employed is that which preserves the cells but does not lead to erroneous results in a subsequent assay. The amount of fixative may depend for example on one or more of the nature of the fixative and the nature of the cells. In some examples, the amount of fixative is about 0.05% to about 0.15% or about 0.05% to about 0.10%, or about 0.10% to about 0.15% by weight. Agents for carrying out fixation of the cells include, but are not limited to, cross-linking agents such as, for example, an aldehyde reagent (such as, e.g., formaldehyde, glutaraldehyde, and paraformaldehyde); an alcohol (such as, e.g., C1-C5 alcohols such as methanol, ethanol and isopropanol); a ketone (such as a $C3-C_5$ ketone such as acetone); for example. The designations C1-C5 or $C3-C_5$ refer to the number of carbon atoms in the alcohol or ketone. One or more washing steps may be carried out on the fixed cells using a buffered aqueous medium.

If necessary after fixation, the cell preparation may also be subjected to permeabilization. In some instances, a fixation agent such as, an alcohol (e.g., methanol or ethanol) or a ketone (e.g., acetone), also results in permeabilization and no additional permeabilization step is necessary. Permeabilization provides access through the cell membrane to target molecules of interest. The amount of permeabilization agent employed is that which disrupts the cell membrane and permits access to the target molecules. The amount of permeabilization agent depends on one or more of the nature of the permeabilization agent and the nature and amount of the cells. In some examples, the amount of permeabilization agent is about 0.01% to about 10%, or about 0.1% to about 10%. Agents for carrying out permeabilization of the cells include, but are not limited to, an alcohol (such as, e.g., C1-C5 alcohols such as methanol and ethanol); a ketone (such as a C3-C5 ketone such as acetone); a detergent (such as, e.g., saponin, TRITON X-100 (4-(1,1,3,3-Tetramethyl-butyl)phenyl-polyethylene glycol, t-Octylphenoxypolyethoxyethanol, Polyethylene glycol tert-octylphenyl ether buffer, commercially available from Sigma Aldrich), and TWEEN-20 (Polysorbate 20, commercially available from Sigma Aldrich)). One or more washing steps may be carried out on the permeabilized cells using a buffered aqueous medium.

Contact of the sample with the compositions of the invention is continued for a period of time sufficient to achieve binding of the affinity reagent to the target rare molecule in the sample. The period of time may be dependent for example on one or more of the nature and size of the different populations of target rare cells, the nature of the reaction mixture, or the volume to be filtered (optional). In some examples, the period of contact is about 1 minute to about 1 hour, about 5 minutes to about 1 hour, or about 5 minutes to about 45 minutes, or about 5 minutes to about 30 minutes, or about 5 minutes to about 20 minutes, or about 5 minutes to about 10 minutes, or about 10 minutes to about 1 hour, or about 10 minutes to about 45 minutes, or about 10 minutes to about 30 minutes, or about 10 minutes to about 20 minutes, for example.

Assays

The compositions of the invention may be used for conducting an assay that specifically associates the mass tag with the rare molecule. An exemplary assay uses the affinity reagent to specifically bind the rare molecule in the sample. The mass tag is associated with, bound to, the affinity reagent. Upon specific binding of the capture moiety to the target analyte, the mass tag becomes associated with the rare molecule. A separation step is then performed, such as washing away unbound affinity reagent or performing a purification that separates the rare molecule/affinity reagent/mass tag complex from the sample. After the separation step (washing or purification), the mass tag is then eluted from the affinity reagent by breaking the bond of the labeling unit between the affinity reagent and the mass label using a releasing agent as described above. The mass label is then ionized and analyzed. Specifically, an environment can be created that promotes dissociation of the mass tag from the moiety. For example, a pH change can be used to promote dissociation. Alternatively chemical reagents can be used to promote dissociation. Alternatively, heat can be used to promote dissociation. In certain embodiments, a combination of techniques is used, e.g., a combination of pH change and a releasing agent. Binding and release may involve thiol/disulfide chemistry which is well-established in biological chemistry but alternatives like complementary bonding of PNAs (R. J. Ball et al. Artificial DNA: PNA and XNA, 1(2010) 27-35) can be used.

Specific binding or specific association refers to a binding reaction that is determinative of the target analyte of interest in a heterogeneous population of molecules. Thus, under designated conditions (e.g, immunoassay conditions), the specified capture moiety (e.g., antibody variable domain) binds to its particular "target" and does not bind in a significant amount to other molecules present in a sample. The specific binding/association means that binding is selective in terms of target identity, high, medium or low binding affinity or avidity, as selected. Selective binding is usually achieved if the binding constant or binding dynamics is at least 10 fold different.

On the other hand, non-specific binding involves non covalent binding between molecules that is relatively independent of specific surface structures. Non-specific binding may result from several factors including hydrophobic interactions between molecules.

Ion Generation of the Mass Tag

Any approach for generating ions of the mass tag known in the art may be employed. Exemplary mass spectrometry techniques that utilize ionization sources at atmospheric pressure for mass spectrometry include electrospray ionization (ESI; Fenn et al., Science, 246:64-71, 1989; and Yamashita et al., J. Phys. Chem., 88:4451-4459, 1984); atmospheric pressure ionization (APCI; Carroll et al., Anal. Chem. 47:2369-2373, 1975); and atmospheric pressure matrix assisted laser desorption ionization (AP-MALDI; Laiko et al. Anal. Chem., 72:652-657, 2000; and Tanaka et al. Rapid Commun. Mass Spectrom, 2:151-153, 1988). The content of each of these references in incorporated by reference herein its entirety.

Exemplary mass spectrometry techniques that utilize direct ambient ionization/sampling methods including desorption electrospray ionization (DESI; Takats et al., Science. 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), ion generation using a wetted porous material (Paper Spray, U.S. Pat. No. 8,859,956), and electrospray-assisted laser desorption/ionization (ELDI; Shica et al., J. Rapid Communications in Mass Spectrometry, 19:3701-3704, 2005). The content of each of these references in incorporated by reference herein its entirety.

Ion generation can be accomplished by placing the sample on a porous material and generating ions of the mass tag from the porous material or other type of surface, such as shown in Ouyang et al., U.S. patent application publication number 2012/0119079, the content of which is incorporated by reference herein in its entirety. Alternatively, the assay can be conducted and ions generated from a non-porous material, see for example, Cooks et al., U.S. patent application Ser. No. 14/209,304, the content of which is incorporated by reference herein in its entirety). In certain embodiments, a solid needle probe or surface to which a high voltage may be applied is used for generating ions of the mass tag (see for example, Cooks et al., U.S. patent application publication number 20140264004, the content of which is incorporated by reference herein in its entirety).

Ion Analysis

Figure 10:
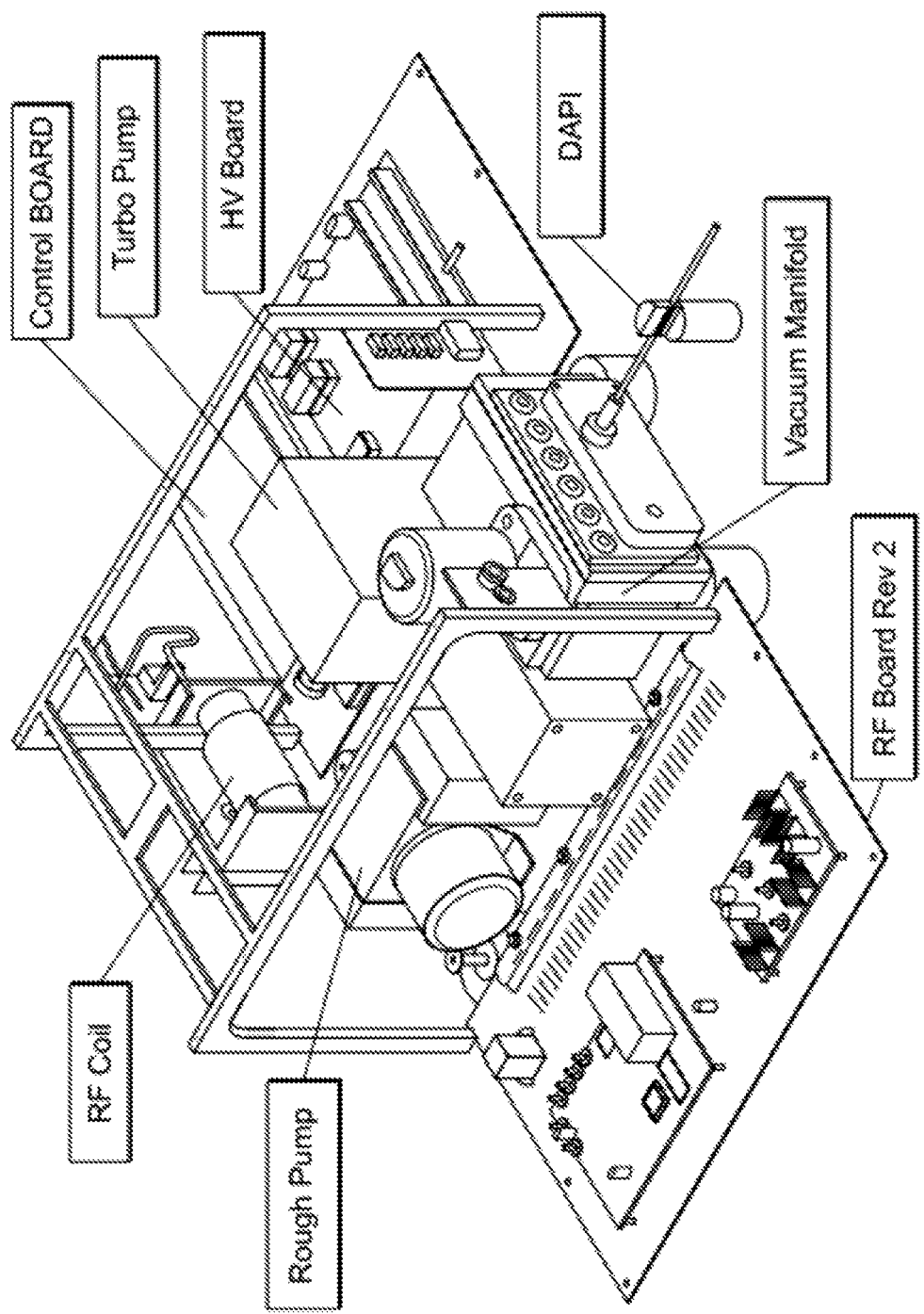
FIG. 10 is a picture illustrating various components and their arrangement in a miniature mass spectrometer.

In certain embodiments, the ions are analyzed by directing them into a mass spectrometer (bench-top or miniature mass spectrometer). FIG. 10 is a picture illustrating various components and their arrangement in a miniature mass spectrometer. The control system of the Mini 12 (Linfan Li, Tsung-Chi Chen, Yue Ren, Paul I. Hendricks, R. Graham Cooks and Zheng Ouyang "Miniature Ambient Mass Analysis System" Anal. Chem. 2014, 86 2909 2916, DOI: 10.1021/ac403766c; and 860. Paul I, Hendricks, Jon K, Dalgleish, Jacob T, Shelley, Matthew A. Kirlcis. Matthew T. McNicholas, Linfan Li, Tsung-Chi Chen, Chien-Hsun Chen, Jason S. Duncan, Frank Boudreau, Robert J. Noll, John P. Denton, Timothy A. Roach, Zheng Ouyang, and R. Graham Cooks "Autonomous in-situ analysis and real-time chemical detection using a backpack miniature mass spectrometer: concept, instrumentation development, and performance" Anal. Chem., 2014, 86 2900-2908 DOI: 10.1021/ac403765x, the content of each of which is incorporated by reference herein in its entirety), and the vacuum system of the Mini 10 (Liang Gao, Qingyu Song, Garth E. Patterson, R. Graham Cooks and Zheng Ouyang, "Handheld Rectilinear Ion Trap Mass Spectrometer", Anal. Chem., 78 (2006) 5994-6002 DOI: 10.1021/ac061144k, the content of which is incorporated by reference herein in its entirety) may be combined to produce the miniature mass spectrometer shown in FIG. 10. It may have a size similar to that of a shoebox (H20×W25 cm×D35 cm). In certain embodiments, the miniature mass spectrometer uses a dual LIT configuration, which is described for example in Owen et al. (U.S. patent application Ser. No. 14/345,672), and Ouyang et al. (U.S. patent application Ser. No. 61/865,377), the content of each of which is incorporated by reference herein in its entirety.

The mass spectrometer (miniature or benchtop), may be equipped with a discontinuous interface. A discontinuous interface is described for example in Ouyang et al. (U.S. Pat. No. 8,304,718) and Cooks et al. (U.S. patent application publication number 2013/0280819), the content of each of which is incorporated by reference herein in its entirety.

The factors that should control detection sensitivity are the combined efficiency of all the steps in the chemistry, the number of tags per affinity reagent, the number of affinity reagents per rare molecule and the number of ions per mass tag, the ionization sensitivity in the MS, the S/N ratio in the MS, the number of different transitions corresponding to different mass tags that are being measured, and the MS acquisition time. However, in ultratrace analysis like this, it is often the magnitude of the chemical noise that determines performance. It is for this reason that in the case of complex mixtures, MS/MS often gives lower detection limits than does the normal MS, even though the total signal in the latter case may be orders of magnitude greater.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The materials used for these Examples were from Sigma-Aldrich Corporation (St. Louis MO) unless otherwise indicated. Antibody conjugates were prepared by standard bioconjugation techniques such as described by Greg T. Hermanson in Bioconjugate Techniques, Third Edition 2013, Elsevier Inc., 225 Wyman Street, Waltham MA. Imidazolium and pyridinium mass labels were prepared by standard Imidazolium synthesis techniques such as described by Michael W. Pennington and Ben M. Dunn in Imidazolium Synthesis Protocols. Edition 1. November 1994, Springer-Verlag. New York, LLC, New York NY. Materials are shown in Table 1 along with common terms used in the description for the material.

Example 1: Method for Quaternary Mass Labeling of Target Rare Molecules

Cancer cells were prepared for reaction with mass labels by washing cultured SKBR human breast cancer cells twice in 1000 µL Phosphate Buffered Saline (PBS) with centrifugation (2 min at 2500 rpm (Eppendorf Centrifuge 5417C)). Both times, the solution was discarded yielding a pellet of cells. The cells are were suspended in 1000 µL PBS with 0.2% Triton X100 (PBST 0.2%) as a permeabilization step and the cells were incubated for 7 minutes followed by washing four times in 1000 µL PBS. The cells are were suspended in 1000 µL casein buffer as a blocking step and the cells were incubated for 7 minutes followed by washing 1 times in 1000 µL PBST 0.05%). The cells are were reacted with 300 µL of a 10 µg/mL CK-8-18 antibody conjugated with Dylight 550 fluorescent label in casein buffer to allow visualization of cancer cells. Cells were incubated for 25 minutes followed by washing 4 times in 1000 µL PBST (0.05%). The cells were reacted with 500 µl of a 1 µg/mL solution of 4,6-diamidino-2-phenylindole (DAPI) to allow visualization of cancer cell nuclei. Cells were incubated for 1 minutes followed by washing 4 times in 1000 µL PBST (0.05%). The stained cell mixture was diluted to 1 mL with PBS, and a 2 μL sample was examined under the microscope to verify a stained cell count were counted (~66500 cells/mL)

Mass labels were prepared by coupling L-carnitine-F-G-G-S-C(QC5-1) and biotin to propylamine functionalized silica and with a cleavable disulfide bond linker arm (i.e. the label binding unit) using the coupling agent N-succinimidyl 3-(2-pyridyldithio)propionate (SPDP). The antibody against the Her-2/neu rare molecule was conjugated to Dylight488 and further conjugated propylamine functionalized silica (nanoparticle, 200 nm, mesoporous pore sized 4 nm) by an amide bond with N-hydroxysuccinimide ester to make the antibody-nanoparticle (the affinity reagent. FIG. 1). Biotin was attached to the affinity reagent with a disulfide bond by the SPDP reaction. The QC5-1 nanoparticle and affinity reagent were conjugated to the streptavidin magnetic bead (Pierce 1%. 0.756 uM at 10 mg/ml) providing 18.2 μg/mL of the combined antibody-QC5-1 particle to make quaternary mass labels attached to affinity reagents. The same method was used to attach other mass labels to the affinity reagents Stained cells were reacted with quaternary mass labels attached to the affinity by adding 300 μL of the 0.075 μg/mL antibody-QC5-1 particles to stained SKBR3 cells (~20,000 cells). The resulting mixture was incubated on a roller mixer at 75 rpm for 2 hours at RT. The mixture was centrifuged and the liquid was decanted followed by washing with 1 mL of PBST (0.3%) twice and 1 mL of PBS twice. The reacted cells were examined under the fluorescent microscope and verify that 100% of SBKR cells were reacted with the antibody-QC5-1 particles. This demonstrated that the quaternary mass labeling method can be used for rare molecule detection.

Example 2: Detection of Quaternary Mass Labeling

A benchtop Linear Ion Trap Mass Spectrometer (LTQ Thermo Fisher) was used to analyze mass label ions produced by nano-electrospray ionization (nESI) to test detection limits (estimated as the concentration giving a signal-to-noise ratio equal to 3). Instrument settings were as follows: spray voltage, 1.5 kV; capillary temperature, 150° C.; tube lens, 65 V; capillary voltage, 15 V; collision energy, 35; Q activation, 0.3.

A list of the compounds tested is presented in Table 1 which includes types of potential mass label with and without quaternary structure and included various 3 amino acid peptides, 6 amino acid peptides, and 9 amino acid peptides as well as a small molecule quaternary imidazolium salt (methylimidazolium-methyl-salicylaldehyde, MIMSA) and quaternary nuclear staining reagent, Nile Blue A. For peptides, the quaternary structure was made by adding an L-carnitine residue to the N-termini. Peptides lacking quaternary structure has detected at a limit of detection of 10 to 50 nM. Adding the quaternary structure improved the limit of detection to 1 nM. This demonstrates that the quaternary mass labels allow greater sensitivity and are ionized readily for detection.

TABLE 1

Mass Labels Limits of Detection by nESI

| Mass Label | Peptide Sequence | Molecular Weight | Limit of Detection (nM) |
|---|---|---|---|
| Mass Labels without quaternary structure | | | |
| IC9-1 | I-G-M-T-S-R-Y-F-C | 1077.3 | 50 |
| IC9-3 | I-G-M-G-S-R-Y-F-C | 1033.2 | 50 |
| RC3-1 | R-G-C | 333.4 | 10 |
| RC3-3 | R-I-C | 389.5 | 10 |
| RC3-4 | R-Y-C | 439.5 | 10 |
| RC3-5 | R-K-C | 404.5 | 10 |
| Mass Labels with quaternary structure | | | |
| QC5-1 | L-carnitine-F-G-G-S-C | 612.7 | 1 |
| QC5-2 | L-carnitine-F-F-S-G-C | 702.8 | 1 |
| QC5-3 | L-carnitine-F-G-T-T-C | 670.8 | 1 |
| QC5-4 | L-carnitine-F-G-T-A-C | 640.8 | 1 |
| MIMSA | N/A | 217.3 | 1 |
| Blue Nile A | N/A | 318.4 | 1 |

Example 3: Methylimidazolium and Pyridinium Analogues of the Quaternary Mass Label Methylimidazolium and pyridinium analogues of the quaternary mass label were synthesized. In order to conjugate such a mass label to propylamine functionalized silica nanoparticles, an imine was formed directly or the nanoparticles were modified with 1,2-diol to form an acetal through the aldehyde functionality of the quaternary mass label. Methylimidazolium and pyridinium analogues were made from salicylaldehyde by first performing a Blanc chloromethylation reaction and then isolating the product for one further reaction with an N-substituted imidazole or a pyridine analogue. Changes to the structure of the N-substituent of the imidazole or the substitution of the pyridine introduced to chloromethylated salicylaldehyde facilitated the synthesis of mass labels with different structures. FIG. 5 shows the methylimidazolium (m/z 217) and pyridinium (m/z 214) mass labels. The mass labels generate unique product ions due fragmentation upon ionization and subsequent analysis by MS/MS, which are represented by methylimidazolium (m/z 83) and pyridinium (m/z 80).

FIG. 6 shows how an affinity reagent or rare molecule represented by R is connected through an acetal or ketal bond the quaternary mass label. The bond is formed by the reaction of a diol connected to R and an aldehyde of the quaternary mass label. A diol is first attached to the amine of the affinity reagent or rare molecule (R) by reaction of ß-hydroxy-γ-butyrolactone to form an amide bond. A detailed procedure for making such materials follows:

The Preparation of Chloromethylsalicylaldehyde

Paraformaldehyde (1 g) was suspended in 12 M hydrochloric acid (4 mL) at room temperature with stirring. The paraformaldehyde powder was allowed to partially solubilize in the acid (so that there was no dry paraformaldehyde floating on top of the liquid) and then salicylaldehyde (0.6 g was added dropwise over the course of half an hour). The resulting mixture adopted a yellow tint which eventually cleared as the paraformaldehyde completely dissolved. The solution was left to stir for 12 hours over which time it lost its color and the product was formed as a white precipitate. The product was filtered and washed three times with deionized water to remove residual acid. The crude material was air-dried and used in the next step without further purification.

Preparation of (Methylimidazole)Methylsalicylaldehyde

Crude chloromethylsalicylaldehyde (1 eq) was dissolved in dichloromethane at room temperature. Methylimidazole (1.5 eq) was added dropwise causing the desired product to precipitate almost immediately (in small portions as the imidazole was added). The precipitate was filtered and washed three times with dichloromethane in order to remove all residual organics (essentially purifying the material).

General Procedure for the Formation of the Imine-Bound Nanoparticle Conjugate Species Methylimidazolium)methylsalicylaldehyde (1.2 eq) was dissolved in anhydrous methanol (1 mL) in an Eppendorf tube. The corresponding amine conjugate partner (1 eq) was added to the Eppendorf tube and the solution was left for 30 min over which time it adopted a yellow color indicating the formation of the imine.

Preparation of the Acetal Protected Imidazolium Mass Label

The imidazolium mass label (0.3 g) was dissolved in anhydrous dimethylformamide and Amberlyst-15 (hydrogen form, mass not measured) was added. Ethylene glycol (0.2 g) was added to the solution once the imidazolium mass label had dissolved and the reaction mixture was left to stir for 6 hours. The structure of the resulting acetal was confirmed by mass spectrometry.

Preparation of Diol Functionalized Propylamine

Propylamine (neat, 1 eq.) was mixed with beta-hydroxy-gamma-butyrolactone (neat 1 equiv.). The reaction proceeded with an immediate exotherm and eventually crystallization followed as the reaction went to completion. The yield was essentially quantitative.

Modification of Propylamine Functionalized Silica Nanoparticles with a Diol

Propylamine functionalized silica nanoparticles (0.03 g) were covered with beta-hydroxy-gamma-butyrolactone (300 µL) in an Eppendorf tube and left to react for an hour. On a larger scale, The reaction produced an exotherm strong enough to be felt on the skin, indicating an amidation reaction akin to that which was observed for free propylamine.

FIG. 5 shows imidazolium (A) and pyridinium (B) analogues of the quaternary mass label produced by this method. The methylimidazolium (m/z 217) and pyridinium (m/z 214) mass labels. In these examples, the mass structure is comprised of all other atoms that are not directly connected through a single bond or by conjugation to the formal positive charge, i.e. the salicylaldehyde moiety and methyl group. The aldehyde of the methyl salicylaldehyde was used to bind the amine of a propylamine functionalized silica nanoparticle through either an imine bond or, following modification of the amine, through an acetal bond as shown in FIG. 3.

The two methods for attachment to the aldehyde were compared. An imine bond (FIG. 3 panel D) and an acetal bond (FIG. 3 panel B) were made using organic amines as models for rare molecules and affinity reagents. Conjugates of MIMSA with propylamine, mercaptoaniline and 1,6-diaminonaphthalene were investigated. The imine bond formed rapidly in anhydrous methanol. The bond was found to cleave readily in the presence of aqueous solvents such as PBS. For the purposes of using these materials in methods, it is important that the bond used to link the quaternary mass label be stable in buffered aqueous solutions typically used in an assay procedure. The imine system was deemed unacceptable due to complete hydrolysis of the bond after a 20 min, exposure time to aqueous solvents. The acetal and materials were almost perfectly stable over at least 20 min.

For the purposes of conjugation to an organic amine through an acetal linkage, the free amines were first functionalized with a 1.2-diol structure by reaction with ß-hydroxy-γ-butyrolactone (See FIG. 6). The reaction scheme was successfully applied to organic amines and amine nanoparticles. It produced the required diol structure (label binding unit, FIG. 1) and showed an effective means to conjugate with aldehyde and ketones of the mass labels. The resulting acetal and ketal had the same hydrolytic stability of an ethylene glycol derived acetal. The acetal and ketal were also and are easily separated from the affinity reagents by simple one step liquid addition of acidified spray solvents such as 50% acetonitrile in water with 0.1% trifluoroacetic acid (TFA). No suppression of the signal from the mass labels in the mass spectrum was observed by nESI from 50% acetonitrile water with 0.1% trifluoroacetic acid (TFA). By comparison, the use of Tris(2-carboxyethyl)phosphine hydrochloride) at 1 mg/mL in water to break disulfide bonds caused suppression of mass labels limits of detection by nESI by 50% or more. Disulfide bonds were therefore not ideal for attachment of quaternary mass labels.

An example workflow incorporating all of the elements discussed above was conducted. The modification of propylamine functionalized silica nanoparticles was carried out with ß-hydroxy-γ-butyrolactone. The methylimidazolium analogue of the mass label (FIG. 5, A) was then bound to the resulting diol functionalized nanoparticles. Following this conjugation and subsequent washing steps, the mass label bound to the nanoparticles was released into a release solution of aqueous trifluoroacetic acid and the released mass label was quantitated using a calibration curve against an internal standard. The internal standard was the pyridinium analogue of the mass label (FIG. 5, B). The calculated concentration of mass label in the release solution was two orders of magnitude greater than that measured from the supernatant of the preceding wash step (FIG. 7).

Figure 8:
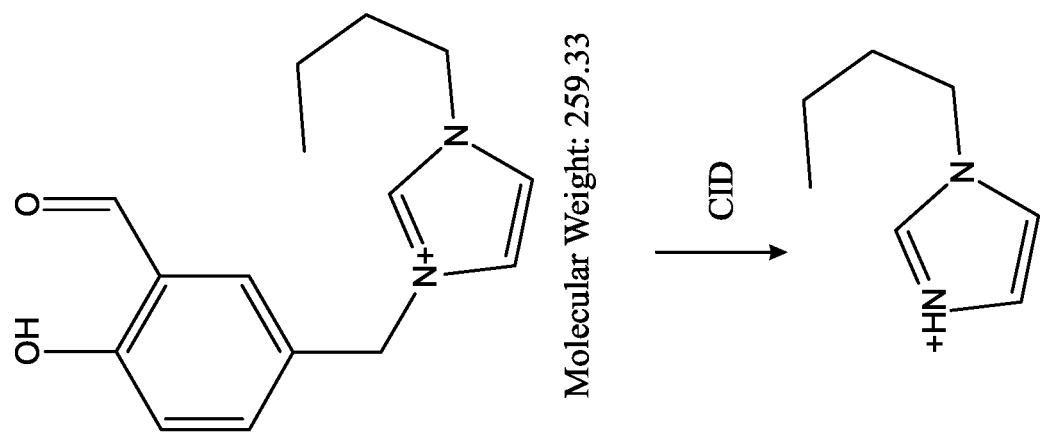
FIG. 8 shows mass labels derived from higher mass analogues of N-substituted imidazoles. The charge unit in these cases is still the quaternary nitrogen, but the variable mass unit has been varied to produce mass labels with different masses.
Figure 8:
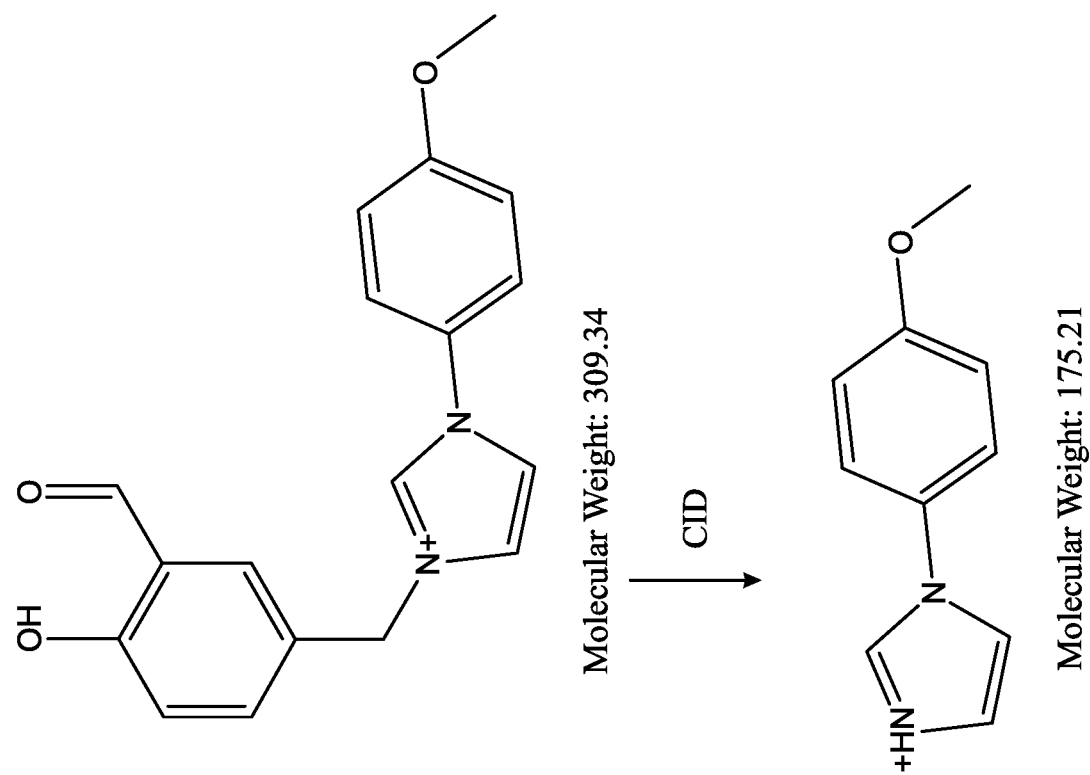

FIG. 8 shows that mass labels with high molecular weight derivatives of imidazolium (m/z 309 and 259) effectively form mass labels with a higher mass Variable Mass Unit. These mass labels also fragmented to yield unique product ions (m/z 175 and m/z 125) which were predictable and analytically separable from the background mass spectrum.

What is claimed is:

1. A method for detecting a target analyte in a sample, the method comprising:
   introducing a charged mass label composition to a sample comprising a target analyte, wherein the charged mass label composition comprises an affinity reagent; and a mass label precursor bound to the affinity reagent, wherein the mass label precursor comprises a label binding unit and a mass label, the label binding unit reversibly binding the mass label to the affinity reagent, wherein the mass label comprises a charge unit chemically coupled to a mass label unit, wherein the mass label unit is neutral and has a pre-defined mass-to-charge-value in a mass spectrum, and wherein upon ionization, the charge unit releases from the mass label unit and the mass label unit is detectable in the mass spectrum due to the mass label unit having the pre-defined mass-to-charge-value in a mass spectrum;

incubating the sample and the charged mass label composition so that the charged mass label composition binds the target analyte via an interaction between the affinity reagent of the charged mass label composition and the target analyte;

releasing the mass label from the affinity reagent by breaking one or more bonds of the label binding unit;

ionizing the mass label; and detecting the ionized mass label and/or fragments thereof in a mass spectrometer, thereby detecting the target analyte in the sample.

2. The method according to claim 1, wherein the sample is a biological sample.

3. The method according to claim 2, wherein the target analyte is a target biological molecule.

4. The method according to claim 3, wherein the target biological molecule is a biomarker related to a disease.

5. The method according to claim 4, wherein the disease is cancer.

6. The method according to claim 1, further comprising quantifying the ionized mass label and/or fragments thereof, thereby quantifying the target analyte in the sample.

7. The charged mass label composition according to claim 1, wherein the pre-defined mass-to-charge-value in the mass spectrum of the mass label or one or more fragments of the mass label is different from background mass-to-charge-values in the mass spectrum.

8. The charged mass label composition according to claim 1, wherein the label binding unit comprises a reversible bond.

9. The charged mass label composition according to claim 8, wherein the reversible bond comprises an acetal or ketal bond.

* * * * *